(12) United States Patent
Kim et al.

(10) Patent No.: US 10,722,388 B2
(45) Date of Patent: Jul. 28, 2020

(54) SOLID-STATE DRAWING METHOD FOR PREPARING A SURGICAL SUTURE OR A BIODEGRADABLE STENT

(71) Applicant: KOREA INSTITUTE OF SCIENCE AND TECHNOLOGY, Seoul (KR)

(72) Inventors: Soo Hyun Kim, Seoul (KR); Young Mee Jung, Seoul (KR); Seung Hyuk Im, Seoul (KR)

(73) Assignee: Korea Institute of Science and Technology, Seoul (KR)

(*) Notice: Subject to any disclaimer, the term of this patent is extended or adjusted under 35 U.S.C. 154(b) by 293 days.

(21) Appl. No.: 15/716,620

(22) Filed: Sep. 27, 2017

(65) Prior Publication Data
US 2018/0344489 A1 Dec. 6, 2018

(30) Foreign Application Priority Data
Jun. 1, 2017 (KR) .................. 10-2017-0068362

(51) Int. Cl.
*A61F 2/91* (2013.01)
*A61L 31/06* (2006.01)
(Continued)

(52) U.S. Cl.
CPC .............. *A61F 2/91* (2013.01); *A61L 17/10* (2013.01); *A61L 17/14* (2013.01); *A61L 31/06* (2013.01);
(Continued)

(58) Field of Classification Search
CPC ........ A61F 2/91; A61F 2/88; A61F 2240/001; A61F 2210/0004; A61L 31/14;
(Continued)

(56) References Cited

U.S. PATENT DOCUMENTS 3,001,851 A * 9/1961 Givens .................... D02J 1/228
 264/193
4,980,957 A * 1/1991 Sussman ................. B29C 55/00
 264/290.5

(Continued)

FOREIGN PATENT DOCUMENTS

KR 10-2016-0134269 A 11/2016

OTHER PUBLICATIONS

Travis L. Callahan et al., "Mechanical properties of commercially available nylon sutures in the United States", Journal of Biomedical Materials Research B: Applied Biomaterials, 2016, pp. 1-5, vol. 00B, Issue 00.

(Continued)

*Primary Examiner* — Jeffrey M Wollschlager
(74) *Attorney, Agent, or Firm* — Rabin & Berdo, P.C.

(57) ABSTRACT

A solid-state drawing method for preparing a surgical suture or a biodegradable stent having improved flexibility and mechanical strength. The method for preparing a biodegradable stent includes (a) providing a biodegradable filament that comprises a material which is biodegradable; (b) solid-state drawing the biodegradable filament to provide a drawn biodegradable filament; (c) shaping the drawn biodegradable filament to provide a shaped biodegradable filament; and (d) annealing the shaped biodegradable filament to provide the biodegradable stent, wherein the biodegradable filament has a draw ratio that ranges from 1.1 to 5.0; and wherein the draw ratio is calculated by Equation 1 below:

Draw ratio=$(L_{SSD}/L_O)^2$, where $L_O$ is length of the biodegradable filament before the solid-state drawing, and $L_{SSD}$ is the length of the biodegradable filament after the solid-state drawing.

4 Claims, 21 Drawing Sheets

(51) Int. Cl.
  A61L 31/14      (2006.01)
  A61L 17/10      (2006.01)
  A61L 17/14      (2006.01)
  D02J 1/22       (2006.01)
  A61F 2/88       (2006.01)
  B29C 71/02      (2006.01)

(52) U.S. Cl.
  CPC .............. *A61L 31/14* (2013.01); *A61L 31/148* (2013.01); *B29C 71/02* (2013.01); *D02J 1/22* (2013.01); *D02J 1/224* (2013.01); *D02J 1/225* (2013.01); *A61F 2/88* (2013.01); *A61F 2210/0004* (2013.01); *A61F 2240/001* (2013.01); *B29C 2071/022* (2013.01)

(58) Field of Classification Search
  CPC ........ A61L 17/14; A61L 17/10; A61L 31/148; A61L 31/06; D02J 1/22–229; B29C 71/02; B29C 2017/022
  See application file for complete search history.

(56) References Cited

U.S. PATENT DOCUMENTS

| | | | | |
|---|---|---|---|---|
| 5,294,389 A * | 3/1994 | Hain | ................ | A61B 17/06166 |
| | | | | 264/103 |
| 2001/0003801 A1 * | 6/2001 | Strecker | ........... | A61B 17/12022 |
| | | | | 623/1.11 |
| 2007/0270941 A1 * | 11/2007 | Headley | .................... | A61F 2/90 |
| | | | | 623/1.38 |
| 2011/0268967 A1 * | 11/2011 | Tam | .......................... | D01F 6/04 |
| | | | | 428/364 |

OTHER PUBLICATIONS

Rahul M. Rasal et al., "Poly (lactic acid) modifications", Progress in Polymer Science, 2010, pp. 338-356, vol. 35.

Subbu Venkatraman et al., "Collapse pressures of biodegradable stents", Biomaterials, 2003, pp. 2105-2111, vol. 24.

Rina Chokshi et al., "Hot-Melt Extrusion Technique: A Review", Iranian Journal of Pharmaceutical Research, 2004, pp. 3-16, vol. 3.

Kazi M. Zakir Hossain et al., "Mechanical, crystallization and moisture absorption properties of melt drawn polylactic acid fibres", European Polymer Journal, 2014, pp. 270-281, vol. 53.

Angela M. Harris et al., "Improving Mechanical Performance of Injection Molded PLA by Controlling Crystallinity", Journal of Applied Polymer Science, 2008, pp. 2246-2255, vol. 107.

Seung Hyuk Im et al., Polyamide and Poly (L-lactic acid) Monofilaments with High Mechanical Strength Fabricated by Solid-State Drawing and Shaped-Annealing Process for Vascular Stent, Poster Session (PO) announcement, Sep. 29, 2016.

Seung Hyuk Im et al., "Biodegradable vascular stents with high tensile and compressive strength: a novel strategy for applying monofilaments via solid-state drawing and shaped-annealing processes", Biomaterial Science, 2017, pp. 422-432, vol. 5.

Seung Hyuk Im et al., "Poly (L-lactic acid) scaffold with oriented micro-valley surface and superior properties fabricated by solid-state drawing for blood-contact biomaterials", Biofabrication, 2016, vol. 8.

* cited by examiner

SOLID-STATE DRAWING METHOD FOR PREPARING A SURGICAL SUTURE OR A BIODEGRADABLE STENT

CROSS-REFERENCE TO RELATED APPLICATIONS

This application claims, under 35 U.S.C. § 119, the priority of Korean Patent Application No. 10-2017-0068362 filed on Jun. 1, 2017 in the Korean Intellectual Property Office, the disclosure of which is incorporated herein by reference in its entirety.

TECHNICAL FIELD

The present disclosure relates to a biodegradable stent and a method for preparing the same, more particularly to a technology of preparing a biodegradable stent with improved flexibility and mechanical strength through a solid-state drawing step and an annealing step.

BACKGROUND

Monofilaments such as polyamide (PA) including nylon-6 and nylon-66, polydioxanone (PDS), poly(ethylene terephthalate) (PET), polyvinylidene fluoride (PVDF), etc. have been industrially used in various fields. In addition to those industrial applications, monofilaments have been widely used as biomaterials such as surgical sutures and meshes (non-patent document 1).

However, despite superior physical properties and strength, the monofilaments described above have been limited to be used for biomaterials due to insufficient biocompatibility and degradability. In order to overcome this problem, biodegradable polymers having ester, amide and ether functional groups have gained interests as biomaterials since the late 1960s in the field of biomedicine due to very superior biodegradability. Among them, the polyester poly (L-lactic acid) (PLLA) has been widely used due to very superior properties as a biomaterial, such as biocompatibility and biodegradability, as well as proven safety (non-patent document 2).

However, despite these many advantages of the biodegradable polymers such as polylactic acid, their use in the field of biomedicine requiring high mechanical strength has been restricted because their mechanical strength tends to lag behind that of non-degradable materials. In particular, because mechanical strength is a very important factor in the applications such as surgical suture and vascular stent, non-degradable materials with high strength have been mainly used in this fields (non-patent document 3).

Accordingly, it is important to improve mechanical strength for wide application of the biodegradable polymers in biomedical fields. In order to improve the mechanical strength of the biodegradable polymers, many processing techniques such as melt extrusion, melt drawing and injection molding have been developed thus far. However, these techniques are disadvantageous in that high temperature is necessary to process the polymers, which may cause loss of molecular weight and physical properties, or a very complicated multi-step process is necessary (non-patent documents 4, 5 and 6).

REFERENCES OF THE RELATED ART

Non-Patent Documents

Non-patent document 1. Callahan, Travis L., et al. *Journal of Biomedical Materials Research Part B: Applied Biomaterials* (2016).

Non-patent document 2. Rasal, Rahul M., Amol V. Janorkar, and Douglas E. Hirt. Progress in polymer science 35.3 (2010): 338-356.

Non-patent document 3. Venkatraman, Subbu, et al. *Biomaterials* 24.12 (2003): 2105-2111.

Non-patent document 4. Chokshi, Rina, and Hossein Zia. *Iranian Journal of Pharmaceutical Research* (2010): 3-16.

Non-patent document 5. Hossain, Kazi M. Zakir, et al. *European Polymer Journal* 53 (2014): 270-281.

Non-patent document 6. Harris, Angela M., and Ellen C. Lee. *Journal of Applied Polymer Science* 107.4 (2008): 2246-2255.

SUMMARY

The present disclosure has been contrived to solve the problems described above and is directed to providing a biodegradable stent with improved flexibility and mechanical strength through a solid-state drawing and an annealing step.

In an aspect, the present disclosure relates to a method for preparing a suture, which includes (a) a step of solid-state drawing a filament.

In another aspect, the present disclosure provides a method for preparing a biodegradable stent, which includes: (a) a step of solid-state drawing a biodegradable filament; and (b) a step of shaping and then annealing the drawn biodegradable filament.

In another aspect, the present disclosure relates to a solid-state drawing apparatus, which includes: two rotary motors which are located on left and right sides and rotate in the same horizontal direction; cylindrical jigs which are formed on the two rotary motors and fix a filament; and a heat treatment oven which is provided between the two rotary motors and heat-treats the filament which is fixed by the jigs and moved by the two rotary motors.

According to the present disclosure, a biodegradable stent with improved flexibility and mechanical strength may be provided through a solid-state drawing and an annealing step.

BRIEF DESCRIPTION OF DRAWINGS

in FIG. 1B, the left image shows a polyamide (PA) monofilament and the right image shows a polylactic acid monofilament].

in FIG. 5C, data are mean±standard deviation (SD) (n=3) and the asterisk denotes significant difference between two groups (p<0.05)].

DETAILED DESCRIPTION OF EMBODIMENTS

Figure 1A:
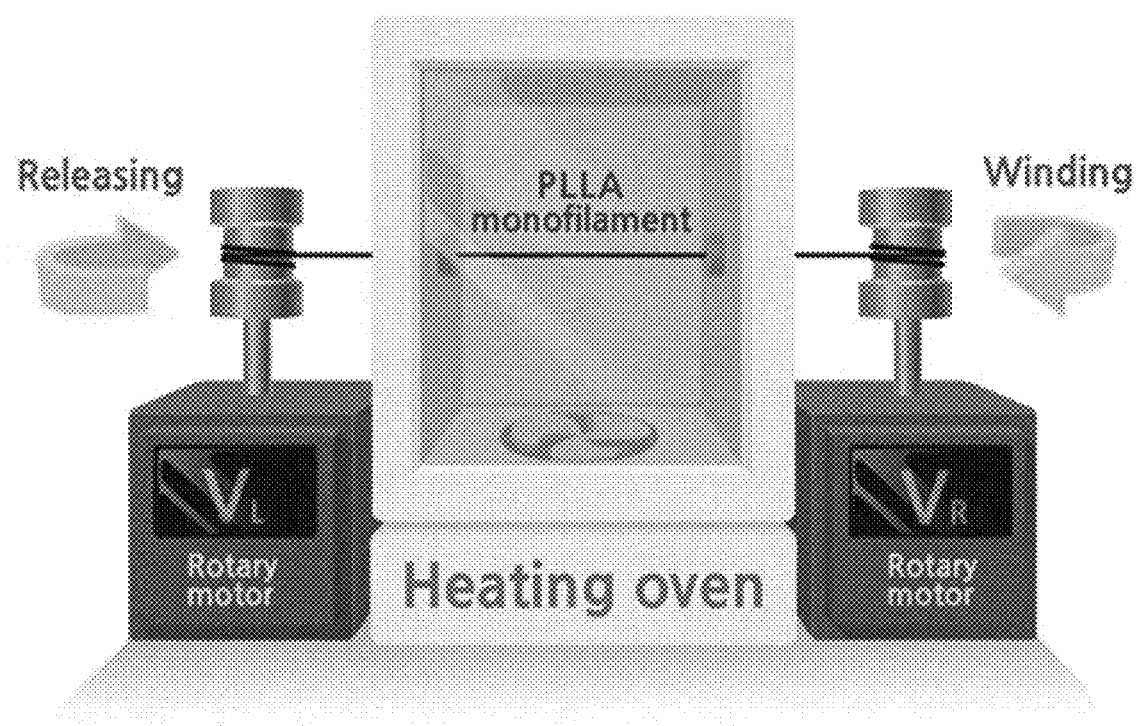
FIG. 1A schematically illustrates a solid-state drawing process according to the present disclosure and FIG. 1B shows a produced monofilament sample [in FIG. 1(a), $V_L$ denotes the rotational velocity of a left motor and $V_R$ denotes the rotational velocity of a right motor.

Hereinafter, various aspects and exemplary embodiments of the present disclosure are described in further detail.

An aspect of the present disclosure relates to a method for preparing a suture, which includes (a) a step of solid-state drawing a filament. Through the method for preparing a suture according to the present disclosure, a biodegradable filament having remarkably improved mechanical strength as compared to the existing non-degradable filament such as polyethylene terephthalate, polyvinylidene fluoride, etc. may be prepared. The method may further include a natural cooling step after the solid-state drawing step.

In an exemplary embodiment of the present disclosure, the filament may be one or more biodegradable filament selected from poly(L-lactic acid) (PLLA), polyglycolic acid (PGA), polycaprolactone (PCL), a lactic acid-glycolic acid copolymer (PLGA; poly(lactic-co-glycolic acid)), poly(trimethylene carbonate) (PTMC), polydioxanone (PDO), chlorinated polylactide (PCL), a PGA-PCL copolymer and a glycolide-caprolactone copolymer (PGCL; poly(glycolide-co-caprolactone)), although not being limited thereto. Specifically, polylactic acid may be used.

In an exemplary embodiment of the present disclosure, the filament may be one or more non-degradable filament selected from polyamide, polyurethane, polyester, polypropylene, polyethylene, a fluorine-based resin and a polyvinyl-based resin, although not being limited thereto. Specifically, polyamide may be used.

In another exemplary embodiment of the present disclosure, a draw ratio of the biodegradable filament or the non-degradable filament may be 1.1-5.0, respectively, and the draw ratio may be calculated by the following Equation 1. When the draw ratios of the filament is within the above range, the prepared suture has very superior flexibility and modulus of elasticity.

$$\text{Draw ratio} = (L_{SSD}/L_O)^2 \quad \text{[Equation 1]}$$

wherein $L_O$ is the length of the filament before the solid-state drawing, and $L_{SSD}$ is the length of the filament after the solid-state drawing.

Another aspect of the present disclosure relates to a method for preparing a biodegradable stent, which includes: (a) a step of solid-state drawing a biodegradable filament; and (b) a step of shaping and then annealing the drawn biodegradable filament.

In the step (a), a biodegradable filament having remarkably improved mechanical strength as compared to the existing non-degradable filament is prepared through solid-state drawing.

Next, the step (b) is a step of fixing the drawn biodegradable filament into a stent shape. As specific examples, one or more biodegradable filament may be fixed by winding around a cylindrical mold having helical or spring-shaped grooves (spring-forming mold) or the filament may be fixed by using a versatile strut-forming mold consisting of 4 rows and 20 columns of fixing screws to form curvatures of desired shape and then the annealing may be performed. However, without being limited thereto, various molds may be mold to shape the filament into desired shapes.

Finally, the method may further include a step of naturally cooling the prepared biodegradable stent and separating the same from the mold. If the biodegradable stent is separated from the mold without cooling, its shape may be deformed.

In an exemplary embodiment of the present disclosure, the biodegradable filament may be one or more selected from poly(L-lactic acid) (PLLA), polyglycolic acid (PGA), polycaprolactone (PCL), a lactic acid-glycolic acid copolymer (PLGA; poly(lactic-co-glycolic acid)), poly(trimethylene carbonate) (PTMC), polydioxanone (PDO), chlorinated polylactide (PCL), a PGA-PCL copolymer and a glycolide-caprolactone copolymer (PGCL; poly(glycolide-co-caprolactone)), although not being limited thereto. Specifically, polylactic acid may be used.

In another exemplary embodiment of the present disclosure, the solid-state drawing may be performed by fixing the biodegradable filament to left and right rotational axes and rotating the left and right rotational axes in the same horizontal direction, such that the right rotational axis is rotated at a higher velocity than the left rotational axis. By controlling the tension applied to the biodegradable filament by controlling the velocity difference of the left and right rotational axes as described above, the biodegradable filament may be drawn in one axis direction.

In another exemplary embodiment of the present disclosure, the ratio of the rotational velocity of the right rotational axis with respect to the left rotational axis may be 1.01-3.0. When the rotational velocity is within this range, the drawn biodegradable filament has remarkably improved tensile strength.

In another exemplary embodiment of the present disclosure, the solid-state drawing may be performed by heat-treating in a heat treatment zone present between the left and right rotational axes and the heat treatment may be performed at a temperature between the glass transition temperature and the melting temperature of the biodegradable filament. Because the heat treatment is performed between the glass transition temperature ($T_g$) and the melting temperature (Tm), loss of molecular weight and physical properties can be decreased relatively as compared to melt processing. In addition, the molecular orientation of the filament can be controlled finely using the tension induced by the drawing.

As a specific example, when polyamide (PA) is used as a suture, the heat treatment may be performed at 45-223° C., specifically at 160-190° C., more specifically at 165-175° C. And, when polylactic acid is used as a biodegradable suture or a biodegradable stent, the heat treatment may be performed at 69-152° C., specifically at 120-150° C., more specifically at 125-135° C.

In another exemplary embodiment of the present disclosure, the biodegradable filament may be heat-treated with an air of the temperature described above. Unlike the existing method of directly heating the sample (thermal heating) in order to increase the mechanical strength of the biodegradable filament, such as melt extrusion, melt drawing or injection molding, the filament can be drawn very safely and simply by providing heat through air heating without using a solvent.

Although not clearly specified in the examples, comparative examples, described below, torsional strength was measured for biodegradable stents prepared from various biodegradable filament while varying the ratio of the rotational velocity of the right rotational axis with respect to the left rotational axis, heat treatment temperature, air heat treatment and passage speed of the biodegradable filament in the heat treatment zone. Also, the roughness of the outer surface was observed by scanning electron microscopy (SEM).

As a result, no breakage occurred after 300 cycles of torsional strength measurement when all the following conditions were satisfied. The outer surface was very smooth initially and no change or defect was observed in the roughness of the outer surface after the 300 cycles of torsional strength measurement.

But, when any one of the following conditions was not satisfied, breakage occurred after the torsional strength measurement and significant defects and roughness change were observed on the outer surface.

(i) biodegradable filament: polylactic acid, (ii) the ratio of the rotational velocity of the right rotational axis with respect to the left rotational axis=1.01-3.0, (iii) heat treatment with air at 120-150° C., (iv) the passage speed of the biodegradable filament in the heat treatment zone=4.3-4.5 mm/min.

In another exemplary embodiment of the present disclosure, a draw ratio of the polylactic acid may be 1.8-2.5 and the draw ratio may be calculated by the following Equation 1. When the draw ratio of the polylactic acid is within the above range, the prepared biodegradable stent has very superior flexibility and modulus of elasticity.

$$\text{Draw ratio}=(L_{SSD}/L_O)^2 \quad \text{[Equation 1]}$$

wherein $L_O$ is the length of the filament before the solid-state drawing, and $L_{SSD}$ is the length of the filament after the solid-state drawing.

Although not clearly specified in the examples, comparative examples, described below, compressive load was measured for biodegradable stents prepared from various biodegradable filament while varying the ratio of the rotational velocity of the right rotational axis with respect to the left rotational axis, heat treatment temperature, air heat treatment, passage speed of the biodegradable filament in the heat treatment zone, annealing temperature, annealing by air heat treatment and annealing time.

As a result, no breakage occurred after 300 cycles of compressive load measurement when all the following conditions were satisfied.

But, when any one of the following conditions was not satisfied, breakage occurred after the compressive load measurement and.

(i) biodegradable filament: polylactic acid, (ii) the ratio of the rotational velocity of the right rotational axis with respect to the left rotational axis=1.01-3.0, (iii) heat treatment with air at 120-150° C., (iv) the passage speed of the biodegradable filament in the heat treatment zone=4.3-4.5 mm/min, (v) annealing by heat treatment with air at 60-100° C., (vi) annealing time=30-180 min.

In another exemplary embodiment of the present disclosure, the biodegradable stent may be in the form of a double spring. When the biodegradable stent is in the form of a double spring, an effect of energy dispersion in response to external force may be achieved because fibers are aligned more closely than when the biodegradable stent is in the form of a helix. In addition, because a twist angle is larger than the helix type, it exhibits stronger resistance to the force applied in the circumferential direction.

Another aspect of the present disclosure relates to a solid-state drawing apparatus, which includes: two rotary motors which are located on left and right sides and rotate in the same horizontal direction; cylindrical jigs which are formed on the two rotary motors and fix a filament; and a heat treatment oven which is provided between the two rotary motors and heat-treats the filament which is fixed by the jigs and moved by the two rotary motors.

As a specific example, after fixing the monofilament to the cylindrical jigs formed on the rotary motors, the filament is released at a specific velocity $V_L$ by the left motor while it is wound at a faster velocity $V_R$ by the right motor than the velocity $V_L$ of the left motor. As a result, the filament fixed to the jigs is drawn because tension is applied thereto due to the difference of $V_L$ and $V_R$.

The filament can be drawn safely without loss of mechanical strength or flexibility through heat treatment with an air in the oven.

In an exemplary embodiment of the present disclosure, a fan may be equipped in the heat treatment oven. During the drawing process, the heating oven equipped with the fan may provide heat uniformly to the filament which moves inside the oven at a temperature between the glass transition temperature ($T_g$) and the melting temperature ($T_m$).

Hereinafter, the examples of the present disclosure will be described in detail referring to the attached drawings.

However, the following examples are for illustrative purposes only and not intended to limit the scope of this disclosure.

Materials and Instruments (1) A medical-grade poly(L-lactic acid) (PLLA) monofilament was provided by Meta Biomed Co. (Cheongju, Korea).

(2) A polyamide (PA, nylon 6) monofilament was purchased from ProStar (Seoul, Korea).

(3) As a non-degradable polyamide (PA) suture used as a control group for the polyamide (PA), BLUE NYLON™ (NB728 for surgery, Ailee Co., Ltd., Korea) was used.

(4) A degradable suture (MONOFIT-L™) prepared from polydioxanone used as a control group for the polylactic acid monofilament was purchased from Ailee Co., Ltd. (Busan, Korea).

(5) For thickness measurement of samples, a digital vernier caliper (Mitutoyo Co., Japan) was used.

Solid-State Drawing

A solid-state drawing apparatus consisting of two rotary motors on left and right sides, two cylindrical jigs fixing a monofilament and a heating oven at the center was fabricated. After fixing a monofilament to the cylindrical jigs equipped at the rotary motors, the monofilament was released at a specific velocity $V_L$ by the left motor while it was wound at a faster velocity $V_R$ by the right motor than the velocity $V_L$ of the left motor. As a result, the monofilament fixed to the jigs was drawn because tension was applied thereto due to the difference of $V_L$ and $V_R$. In addition, the monofilament was uniformly heated by the heating oven equipped with a fan to a temperature between its transition temperature ($T_g$) and melting temperature ($T_m$) while it was moved inside the heating oven. In this experiment, the monofilament with an initial length of 150 cm was drawn with a left motor velocity ($V_L$) of 3.8 mm/min and a right motor velocity ($V_R$) of 5.2 mm/min. The orientation of the monofilament could be controlled by the degree of drawing, which was defined as the draw ratio (DR). The draw ratio of the sample was calculated by the following Equation 1. After the solid-state drawing, all the samples were left to cool to room temperature and then separated from the apparatus.

$$\text{Draw ratio} = (L_{SSD}/L_O)^2 \quad \text{[Equation 1]}$$

wherein $L_O$ is the length of the filament before the solid-state drawing, and $L_{SSD}$ is the length of the filament after the solid-state drawing.

Annealing (Shape Annealing)

Two types of molds for use in an annealing process were fabricated. A versatile strut-forming mold, consisting of four rows and twenty columns of fixing screws (#2 mm) can prepare monofilament curvatures of desired shapes.

The second mold, a rod-shaped (2 mm) spring-forming mold onto which solid-state drawn monofilaments could be fixed on both sides, was used for the fabrication of double-helix, single spring, and double spring shapes using one and two monofilaments, respectively.

Monofilaments were fixed on the molds and heated in a heating oven for 2 hours at an annealing temperature. The monofilaments were left to cool naturally to room temperature and finally then separated from the molds.

Measurement of Mechanical Properties (1) Tensile Test

The mechanical strength of the filament was measuring using the 5966 universal testing machine (Instron, Norwood, Mass.) according to the international standard ASTM D2256. The tensile extension speed was 10 mm/min.

(2) Compression Test

The mechanical strength of the spring-shaped sample was measured using the 5966 universal testing machine according to the international standard ISO 25539-2; cardiovascular implants; endovascular devices; vascular stents. The compression speed was 10 mm/min and the compression force was removed after sample was compressed to 60% of its inner diameter. The recovery rate of each sample was determined according to the following Equation 2.

$$\text{Recovery rate}(\%) = D_C/D_O \times 100 \quad \text{[Equation 2]}$$

wherein $D_O$ is the inner diameter of the original sample before the compression test and $D_C$ is the inner diameter of the original sample after the compression test.

Scanning Electron Microscopic (SEM) Analysis

The surface morphology of the PLLA monofilament was observed by scanning electron microscopy (SEM) (S-4200, Hitachi, Tokyo, Japan) using an acceleration voltage of 15 kV. The sample was coated with Pt by sputtering using a current of 15 mA for 60 seconds.

Treatment with NaOH

The sample was pretreated with in a 37° C. incubator with 3 M NaOH for 1 hour. After the pretreatment with NaOH, the treated sample was washed 3 times with PBS (pH 7.4) and then immersed in PBS (pH 7.4) in a tube closed with a screw cap. The tube was maintained at 37° C. in an incubator. At the selected point in time, the monofilament was completely rinsed with distilled water and dried in an oven at 37° C. for 12 hours. Then, a sample was prepared for analysis.

Atomic Force Microscopic (AFM) Analysis

For AFM analysis, the NaOH-treated sample was dried by accelerated hydrolysis for 6 weeks. AFM observation was performed in a non-contact (tapping) mode using the XE-100 model equipped with a non-contact cantilever (Park Systems, Suwon, Korea) with a high resonance frequency. $R_q$ (standard deviation of heights) and $R_{pv}$ (peak-to-valley distance) were used as surface roughness indices.

Energy-Dispersive X-Ray Spectroscopic (EDS) Analysis

A sample for use in EDS analysis was selected based on the result of accelerated hydrolysis for 6 weeks. Before the measurement, the sample was washed 3 times with PBS (pH 7.4) and then dried in an oven at 37° C. for 12 hours. The EDS analysis was performed during the SEM imaging of the monofilament.

Wide-Angle X-Ray Diffraction (WAXD) Analysis

Wide-angle X-ray diffraction analysis was performed using the D/MAX-2500/PC X-ray diffractometer (Rigaku, Tokyo, Japan) at room temperature. WAXD data were gathered from 50 to 350. Two-dimensional WAXD (2D-

WAXD) patterns were analyzed using D8 DISCOVER with the GADDS software, mounted with the VANTEC-500 two-dimensional area detector (Bruker, Billerica, Mass., USA). Monochromatized Cu Kα (λ=1.5418 Å) radiation was utilized for all experiments via a transmission method. A typical sample-to-detector distance of 15 cm was used, and the generator settings were 40 kV and 40 mA. An exposure time of 5 min was applied. The sample was positioned in a direction perpendicular to the radiation beam.

Differential Scanning Calorimetric (DSC) Measurement

Differential scanning calorimetric measurement was performed using the Q10 DSC instrument (TA Instruments, New Castle, Del., USA) with nitrogen gas for purging. A sample of about 10 mg was used and the heating rate was 10° C./min. A provided software was utilized for thermogram analysis. The DSC instrument was periodically calibrated using standards. The crystallinity of the sample was calculated according to the following Equation 3.

$$X_c(\%) = \Delta H_m / \Delta H° \times 100 \quad \text{[Equation 3]}$$

wherein $\Delta H_m$ is the enthalpy of fusion and $\Delta H°$ is the theoretical enthalpy of fusion of 100% crystalline PLA (=93.1 J/g).

Statistical Analysis

The results of quantitative analysis were represented as mean±standard deviation (n=3 or 5). Statistical analysis was performed using a one-way analysis of variance, followed by Student's t-test. A value of p<0.05 was considered to be statistically significant.

Experimental Result

Figure 1B:
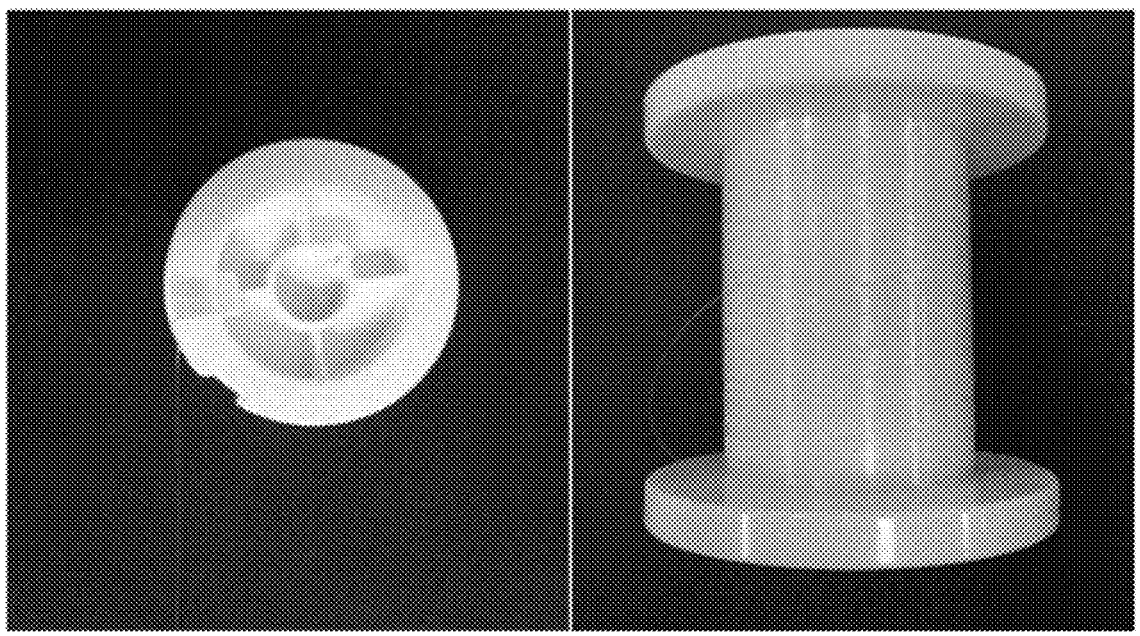

Confirmation of Improvement in Mechanical Strength by Solid-State Drawing Using Polyamide (PA) Monofilament In order to confirm the effect of the improvement in polymer strength by solid-state drawing, a polyamide (PA) monofilament (nylon 6) frequently used industrially [see FIG. 1B, left)] was subjected to solid-state drawing. The solid-state drawing process is schematically illustrated in FIG. 1A.

Figure 2A:
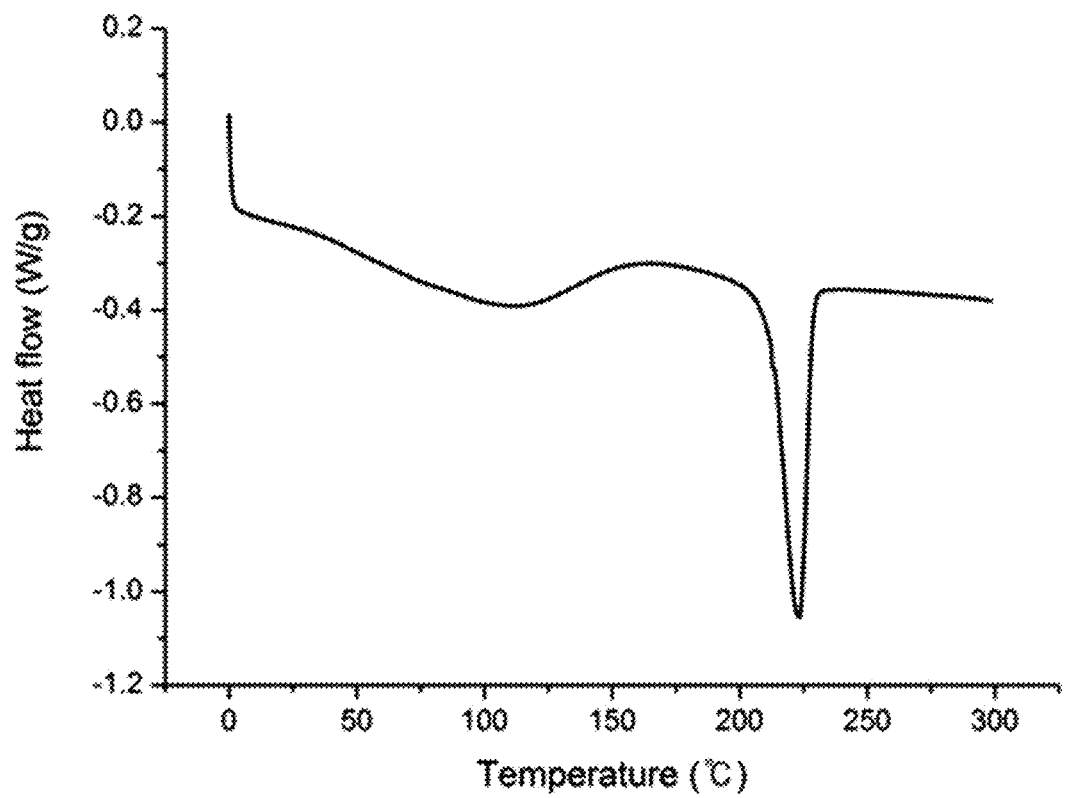
FIG. 2A shows a differential scanning calorimetric (DSC) measurement result of a polyamide (PA) monofilament.
Figure 2B:
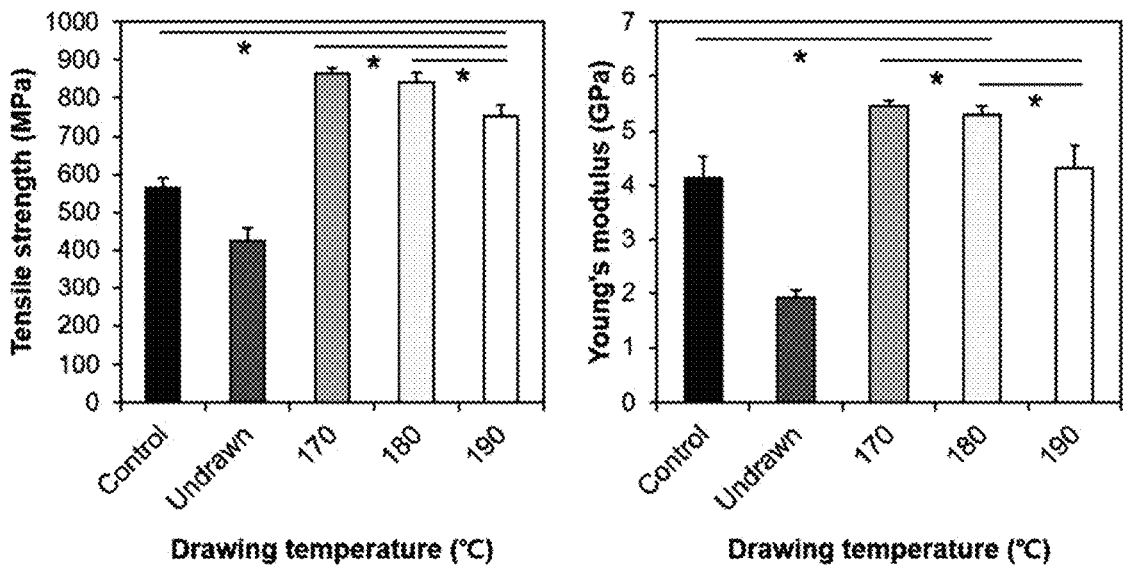
FIG. 2B shows a result of measuring the tensile strength (left) and modulus of elasticity (right) of a polyamide (PA) monofilament depending on a solid-state drawing temperature and FIG. 2C shows a result of measuring tensile strength (left) and modulus of elasticity (right) depending on a draw ratio [data are mean±standard deviation (SD) (n=5); the asterisk denotes significant difference between two groups ($p<0.05$)].

Prior to the solid-state drawing, the thermal properties of the polyamide (PA) monofilament were analyzed to determine the appropriate drawing temperature for the sample by differential scanning calorimetry (DSC). As shown in FIG. 2A, the polyamide (PA) had glass transition temperature ($T_g$) of 45° C. and a melting temperature ($T_m$) of 223° C. similarly to common polyamide (PA). Therefore, the solid-state drawing was performed at 160, 170, 180 and 190° C., all below the melting temperature, with a draw ratio fixed to 3.6. The monofilament broke during the solid-state drawing when the temperature was 160° C. or lower (see Table 1). It is thought that the polymer chains of the PA monofilament could not endure tension at 160° C. or lower because they were in an unstable glass transition phase, as the DSC curve shows. It can be seen that, although the glass transition temperature ($T_g$) of the material is 45° C., the curve changes up to around 150° C. As shown in FIG. 2B, the tensile strength of the solid-state drawn monofilament drawn at 170, 180 and 190° C. was measured to be 863, 840 and 754 MPa, respectively. Thus, the monofilament solid-state drawn at 170° C. had a tensile strength more than two-fold that of the undrawn monofilament (426 MPa). The tensile strengths of all the solid-state drawn monofilaments were higher than that of the commercial PA suture (control, 564 MPa).

In addition, the modulus of elasticity (Young's modulus) was significantly increased by the solid-state drawing for all the processing temperatures. The moduli of elasticity of the solid-state drawn monofilaments drawn at 170, 180 and 190° C. were 5.44, 5.28 and 4.30 GPa, respectively, which were significantly increased compared to those of the control (4.13 GPa) and the monofilament prior to the solid-state drawing (undrawn monofilament, 1.92 GPa). With regard to the various drawing temperatures, the effect of the solid-state drawing on both tensile strength and modulus of elasticity was significantly diminished at 190° C., at which point the polymer started melting. It is thought that the partly melted polymer chains could be oriented less by the solid-state drawing and interrupted the orientation of other polymer chains in one axis direction. The optimal drawing temperature of the polyamide (PA) monofilament at which the best improvement effect can be obtained was 170° C.

Next, experiment was performed to investigate the effect of a draw ratio on the improvement of mechanical strength of the solid-state drawn polyamide (PA) monofilament. As a result, polyamide (PA) monofilament drawn at 170° C. broke during the solid-state drawing when the draw ratio was 4 or greater [see Table 1]. It is thought that, since the time of tension applied to the monofilament increases with increased draw ratio, the polyamide (PA) monofilament could not withstand the long drawing time of 1071 minutes required for the draw ratio of 4 and ultimately broke.

Figure 2C:
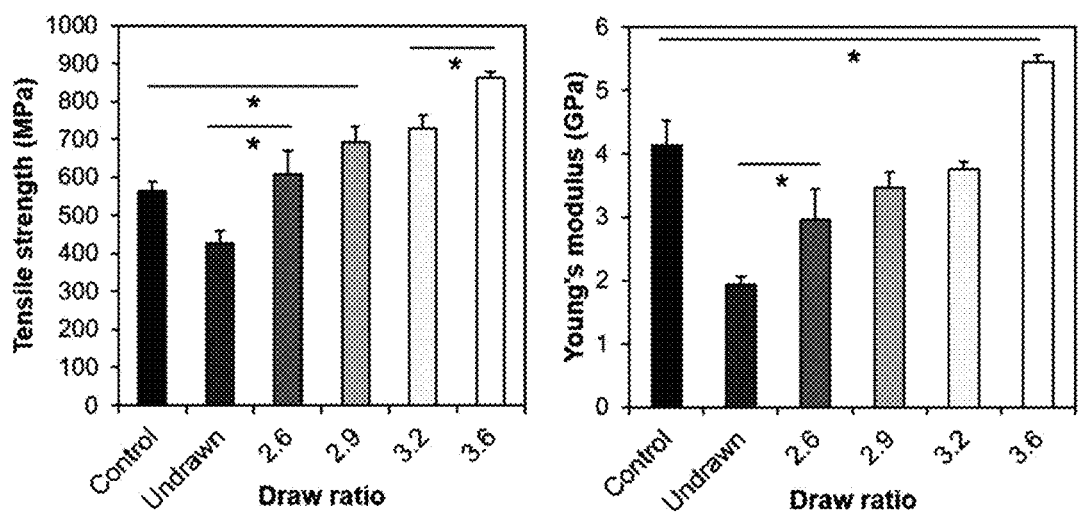

And, as shown in FIG. 2C, the solid-state drawn monofilaments with draw ratios of 2.6, 2.9, 3.2 and 3.6 exhibited considerably increased tensile strengths as compared to the undrawn filament (426 MPa) and higher than that of the control (564 MPa) when the draw ratio was 2.9 (693 MPa) or greater. The improvement in tensile strength was higher with increased draw ratio, with values of 608, 693, 727 and 863 MPa for draw ratios of 2.6, 2.9, 3.2 and 3.6, respectively. The modulus of elasticity was also improved significantly by the solid-state drawing as compared to the undrawn monofilament (1.92 GPa), with 2.97, 3.46, 3.75 and 5.44 GPa for draw ratios of 2.6, 2.9, 3.2 and 3.6, respectively.

Since the polyamide (PA) monofilament solid-state drawn with a draw ratio of 3.6 has a higher modulus of elasticity than the undrawn monofilament, it can be seen that it has more improved mechanical properties for use in surgical suturing, which requires strong closure of wounds. In addition, the thickness of the polyamide (PA) filament could be reduced by the solid-state drawing and the thickness of the polyamide (PA) monofilament became smaller as the draw ratio was increased [see Table 1].

It is to be noted that the solid-state drawn monofilament has a smaller thickness but has higher mechanical strength at the same time.

TABLE 1

| Sample type | Draw ratio | Drawing temperature (° C.) | Thickness (μm) | Breakage |
|---|---|---|---|---|
| Polyamide (PA) monofilament | Undrawn (control) | — | 280 | — |
| | 2.6 | 170 | 260 | — |
| | 2.9 | 170 | 250 | — |
| | 3.2 | 170 | 250 | — |
| | 3.6 | 160 | — | Broken |
| | 3.6 | 170 | 230 | — |
| | 3.6 | 180 | 240 | — |
| | 3.6 | 190 | 230 | — |
| | 4 | 170 | — | Broken |
| | 4.4 | 170 | — | Broken |
| Polylactic acid (PLLA) monofilament | Undrawn (control) | — | 180 | — |
| | 1.2 | 130 | 160 | — |
| | 1.5 | 130 | 150 | — |

TABLE 1-continued

| Sample type | Draw ratio | Drawing temperature (° C.) | Thickness (μm) | Breakage |
|---|---|---|---|---|
| | 2 | 120 | — | Broken |
| | 2 | 130 | 130 | — |
| | 2 | 140 | 130 | — |
| | 2 | 150 | 140 | — |
| | 2.3 | 130 | — | Broken |
| | 2.3 | 140 | — | Broken |
| | 2.3 | 150 | — | Broken |
| | 2.6 | 130 | — | Broken |

Confirmation of Improved Mechanical, Physical and Surface Chemical Properties of Solid-State Drawn Biodegradable Monofilament (1) Improved Mechanical Strength of Solid-State Drawn Monofilament Solid-state drawing was performed to improve the mechanical and physical properties of the biodegradable polylactic acid (PLLA) monofilament, which is the most frequently used biomaterial. In order to optimize the drawing temperature of PLLA which has a glass transition temperature of about 69° C. and a melting temperature of about 152° C., solid-state drawing was performed with a draw ratio fixed to 2 at 120, 130, 140 and 150° C. between the glass transition temperature and the melting temperature. The polylactic acid monofilament broke during the solid-state drawing at the drawing temperature of 120° C. The mechanical strength for other temperature conditions is compared in Table 1.

Figure 3A:
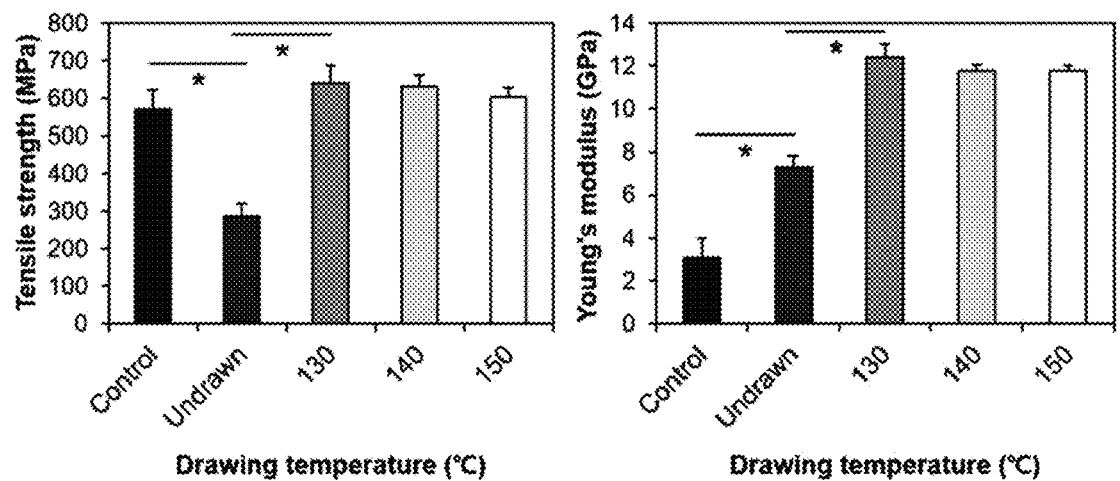
FIG. 3A shows a result of measuring the tensile strength (left) and modulus of elasticity (right) of a polylactic acid monofilament depending on a solid-state drawing temperature.

As shown in FIG. 3A, the solid-state drawing filaments showed significantly improved tensile strength and modulus of elasticity as compared to the undrawn monofilament (287 MPa and 7.3 GPa, respectively) for all the temperature conditions.

For more effective comparison, a commercial polydioxanone (PDS) suture was used as a control synthetic absorbable suture. The polydioxanone suture was the first successfully commercialized absorbable suture and can be degraded into hydroxyethoxyacetic acid by hydrolysis, similar to polylactic acid [see Ray, J. A., et al. *Surgery, Gynecology & Obstetrics* 153.4 (1981): 497-507.]. It is well-known that the polylactic acid suture has good mechanical properties and it has commonly been compared to polylactide (PLA) as an absorbable biomaterial [see Szycher, Michael. A Complete Guide to Medical and Pharmaceutical Applications. CRC Press, 1991.].

The polydioxanone suture had a higher tensile strength (537 MPa) than the undrawn polylactic acid (PLLA) monofilament (287 MPa). However, the polylactic acid monofilament solid-state drawn according to the present disclosure with a draw ratio of 2 showed slightly higher strength than the commercial suture.

The tensile strengths of the monofilaments solid-state drawn at 130, 140 and 150° C. were 639, 630 and 604 MPa, respectively, and the moduli of elasticity were 12.38, 11.75 and 11.77 GPa, respectively. No significant difference was observed between the monofilaments solid-state drawn at different temperatures, but the effect on the improvement of mechanical strength was slightly decreased with an increase in the drawing temperature. It is thought that the effect of improving mechanical strength decreases as the temperature is increased to 150° C. because the temperature is close to the melting temperature of polylactic acid (152° C.) and the polymer begins to be melted, similarly to the case for polyamide (PA). Through this result, the optimal drawing temperature for improving the mechanical strength of the polylactic acid monofilament could be determined to be 130° C.

In order to determine the effect of mechanical strength improvement by solid-state drawing depending on the draw ratio, solid-state drawing was performed with a drawing temperature fixed at 130° C. with draw ratios of 1.2, 1.5, 2, 2.3 and 2.6. As a result, the polylactic acid monofilament broke during the solid-state drawing when the draw ratio was 2.3 or greater [see Table 1]. It is though that the polylactic acid monofilament could not endure the drawing tension for more than 557 minutes, required for the draw ratio of 2.3, similarly to the case for polyamide (PA) monofilament. The reason for the lower maximum draw ratio for the polylactic acid monofilament compared to that for the polyamide (PA) monofilament is likely that drawing is more difficult for polylactic acid than for polyamide (PA), because it has a higher modulus of elasticity. That is to say, it is thought that polyamide (PA) can be drawn with a higher draw ratio because it can be more easily elongated than polylactic acid.

Figure 3B:
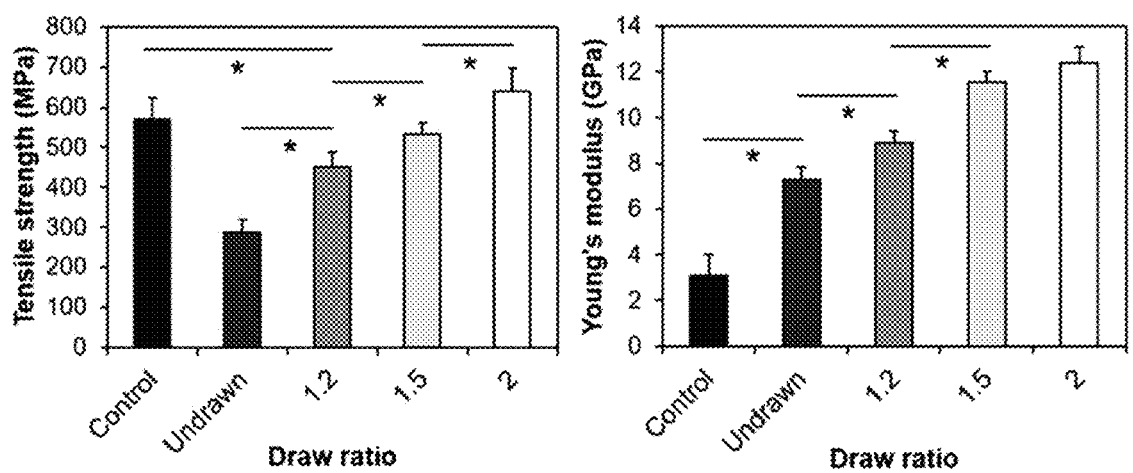
FIG. 3B shows a result of measuring tensile strength (left) and modulus of elasticity (right) depending on a draw ratio [data are mean±standard deviation (SD) (n=5); the asterisk denotes significant difference between two groups (p<0.05)].

As shown in FIG. 3B, the tensile strengths of the solid-state drawn monofilaments with draw ratios of 1.2, 1.5 and 2 were 452, 534 and 639 MPa, respectively. The solid-state drawn monofilaments showed significantly improved tensile strength under all draw ratio conditions than that of the undrawn monofilament (287 MPa), and the values increased as the draw ratio increased.

The solid-state drawn monofilaments with draw ratios of 2 or greater had tensile strengths greater than that of the control group. In addition, the solid-state drawn monofilaments had moduli of elasticity than the undrawn monofilament (7.30 GPa), and the values increased with an increase in the draw ratio, with 8.92, 11.54 and 12.38 GPa for the draw ratios of 1.2, 1.5 and 2, respectively.

To conclude, it was confirmed that the mechanical strength of the polylactic acid monofilament can be significantly improved through the solid-state drawing method according to the present disclosure and a polylactic acid suture with excellent mechanical strength as compared to that of the polydioxanone monofilament commonly used as a suture can be prepared therefrom.

(2) Change in Physical Properties of Polylactic Acid Monofilament by Solid-State Drawing It is commonly known that polylactic acid can have three types of crystal forms, dependent on drawing induced by external forces and the crystallization conditions. The most common α-crystal form presents as a 10/7 helical chain conformation in an orthorhombic unit cell, and can normally be induced by crystallization from glass, melt or solution [Okutani Y, Okumura K, Kawaguchi A. *J Macromol Sci Part B* 2003; B42: 875.; Hoogsteen, W, et al. *Macromolecules* 23.2 (1990): 634-642.; Eling, B., S. Gogolewski, and A. J. Pennings. *Polymer* 23.11 (1982): 1587-1593.; Kobayashi J, Asahi T, Ichiki M, Oikawa A, Suzuki H, Watanabe T, et al. *Journal of Applied Physics.* 1995; 77: 2957-73.; Miyata T, Masuko T. *Polymer.* 1997; 38: 4003-9.; Miyata T, Masuko T *Polymer.* 1998; 39: 5515-21.].

The second form, β-crystal, presents as a 3/2 helical conformation in an orthorhombic or trigonal unit cell and can generally be produced by drawing of semi-crystalline films composed of the α-crystal [Hoogsteen, W, et al. *Macromolecules* 23.2 (1990): 634-642.; Sawai D, Takahashi K, Imamura T, Nakamura K, Kanamoto T, Hyon S H. *Journal of Polymer Science Part B: Polymer Physics.* 2002; 40: 95-104; Sawai D, Takahashi K, Sasashige A, Kanamoto T, Hyon S-H. *Macromolecules.* 2003; 36: 3601-5.]. In addition, it is known that β-crystal is produced by drawing at a higher temperature and a higher draw ratio and α-crystal is produced by drawing at a lower temperature and a lower draw ratio [Eling, B., S. Gogolewski, and A. J. Pennings. *Polymer* 23.11 (1982): 1587-1593.; Hoogsteen, W., et al. *Macromolecules* 23.2 (1990): 634-642.; Leenslag J, Pennings A. *Polymer.* 1987; 28: 1695-702.]. In general, most of the drawn polylactic acid has both α- and β-crystals simultaneously.

The last form, γ-crystal, presents as two packed antiparallel 3/2 helical conformations in an orthorhombic unit cell and can be induced by epitaxial crystallization [Cartier L, Okihara T, Ikada Y, Tsuji H, Puiggali J, Lotz B. *Polymer.* 2000; 41: 8909-19.; Kawai T, Rahman N, Matsuba G, Nishida K, Kanaya T, Nakano M, et al. Crystallization and melting behavior of poly(L-lactic acid). *Macromolecules.* 2007; 40: 9463-9.].

In order to investigate how the mechanical properties of the polylactic acid monofilament are greatly improved by the solid-state drawing according to the present disclosure, the internal crystal structure of the solid-state drawn monofilament was analyzed.

Figure 4A:
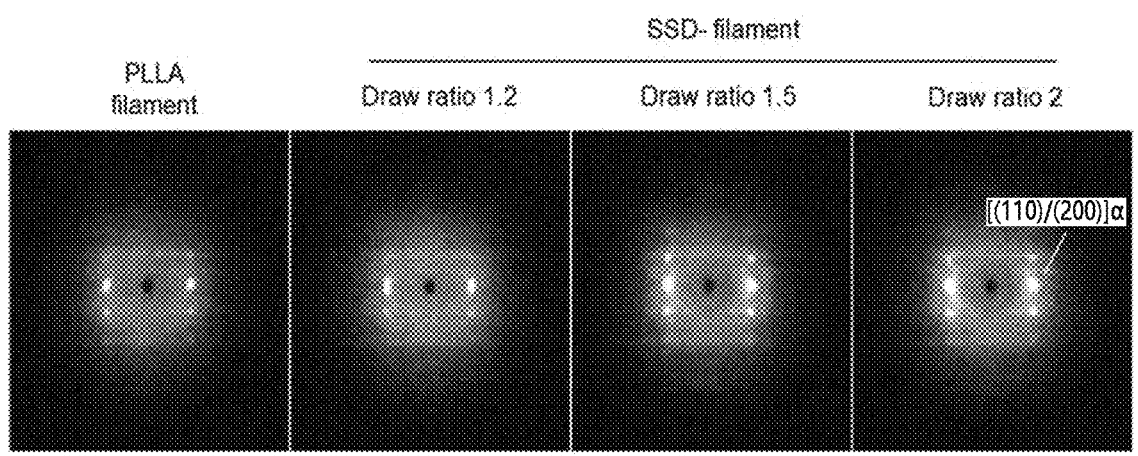
FIG. 4A shows a 2-dimensional wide-angle X-ray diffraction (WAXD) patterns of a polylactic acid monofilament depending on a draw ratio of solid-state drawing.

As seen from the 2-dimensional wide-angle X-ray diffraction pattern of FIG. 4A, the undrawn polylactic acid monofilament already shows anisotropic intensity around the equator. The solid-state drawn monofilament shows strong intensity of (110)/(200) reflection as the draw ratio increases. This means that the solid-state drawing maximizes the internal orientation of the polylactic acid monofilament which has been already oriented in one axis direction.

Figure 4B:
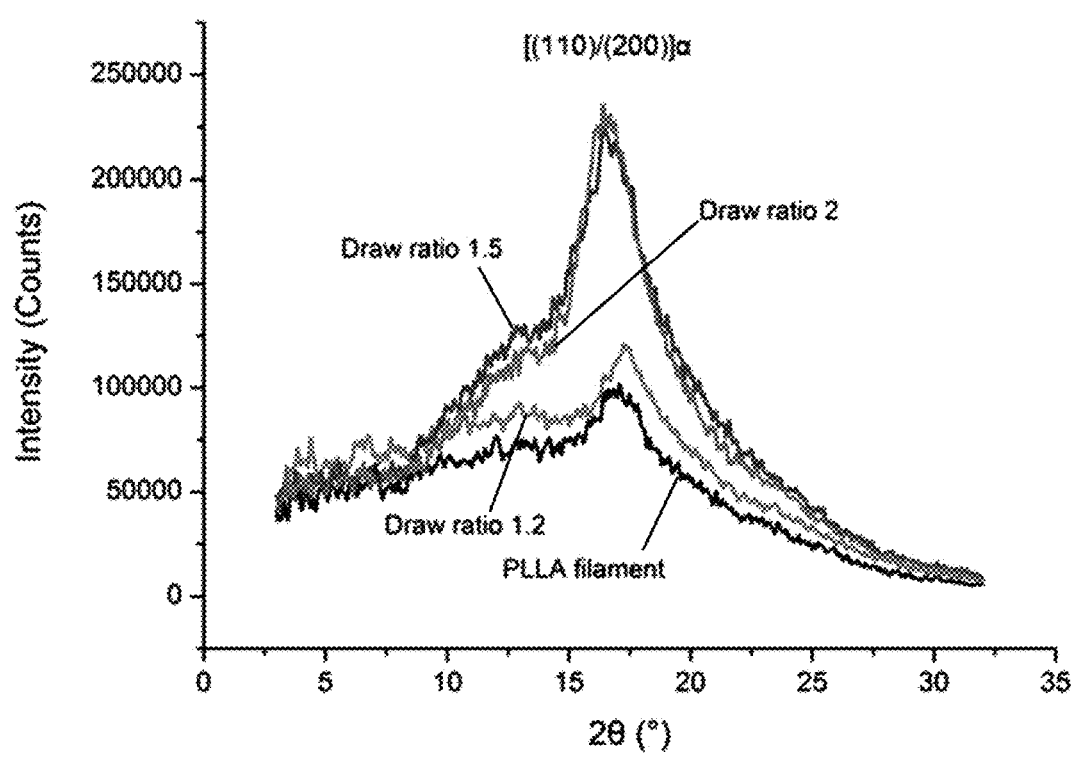
FIG. 4B shows WAXD intensity at 28.

Also, FIG. 4B shows that the peak intensity of the polylactic acid monofilament around 2θ=16.5° increases with the draw ratio compared to the undrawn monofilament. This also confirms that the solid-state drawing induces crystal growth in a specific orientation inside the polylactic acid monofilament.

Figure 4C:
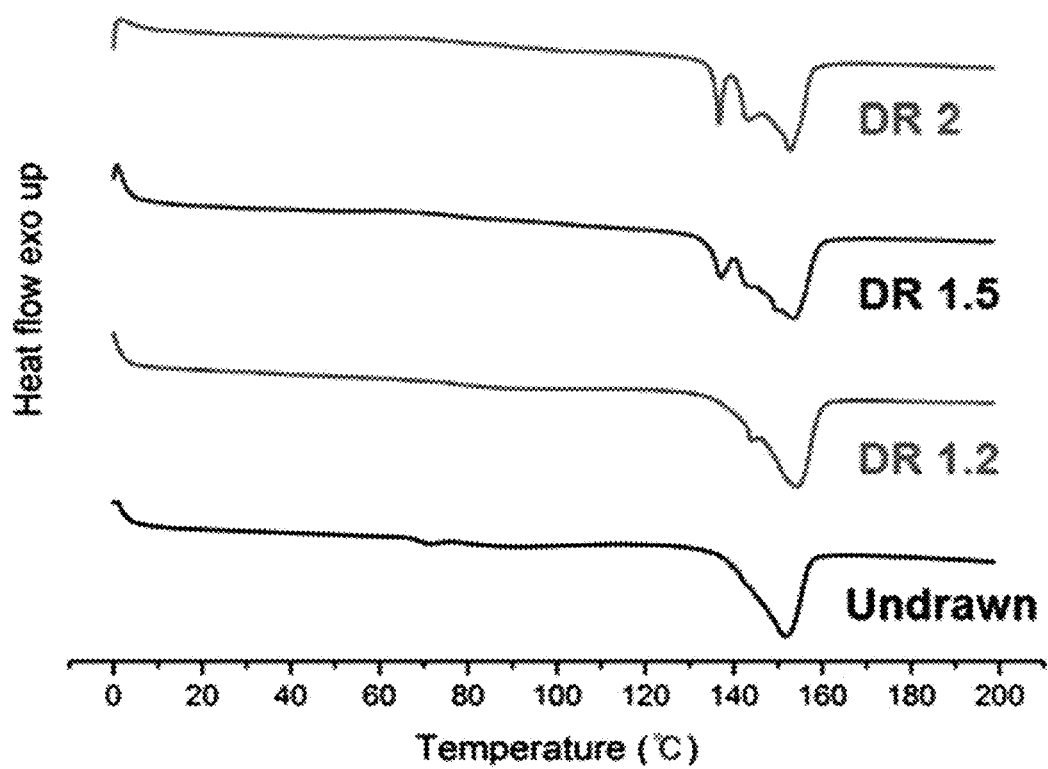
FIG. 4C shows a differential scanning calorimetric (DSC) measurement of a polylactic acid monofilament depending on a draw ratio and FIG. 4D shows crystallinity ($X_c$) depending on a draw ratio [data are mean±standard deviation (SD) (n=3); the asterisk denotes significant difference between two groups (p<0.05)].

As shown in FIG. 4C, the undrawn monofilament had a melting point of about 152° C., while the solid-state drawn monofilament with a draw ratio of 1.2 exhibited a minor melting peak around 144° C. In the solid-state drawn monofilament with a draw ratio of 1.5, the area of the new melting peak was shifted to a lower temperature around 137° C. and the peak area was increased. When the draw ratio was 2, the intensity of the melting peak at 137° C. was increased further without change in the peak position and each melting peak became more distinct. It is thought that, although the polylactic acid monofilament was drawn at a relatively low temperature of 130° C., the new melting peak appeared around 137° C. because β-crystals were newly formed at a high draw ratio [see Sawai, Daisuke, et al. *Journal of Polymer Science Part B: Polymer Physics* 40.1 (2002): 95-104.]. When the draw ratio was 1.5 and 2, a weak melting peak appeared around 143° C.

Figure 4D:
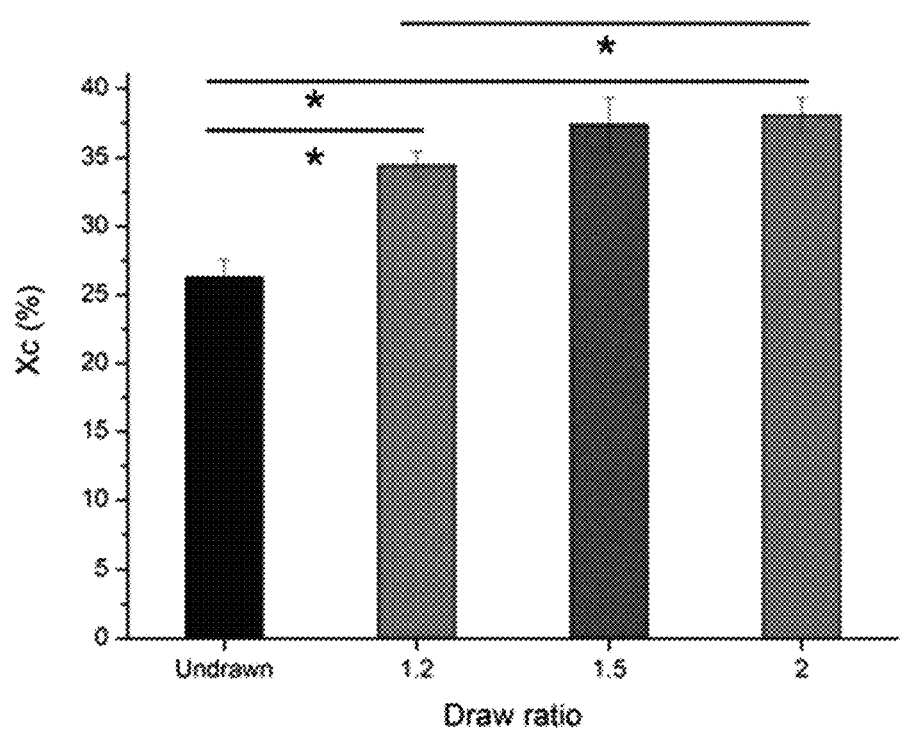

As shown in FIG. 4D, the solid-state drawn monofilaments with draw ratios of 1.2, 1.5 and 2 had a crystallinity ($X_c$) of 34.4±1.0, 37.4±2.0 and 38.0±1.3%, respectively, while the undrawn monofilament had an $X_c$ of 26.3±1.3%.

Figure 5A:
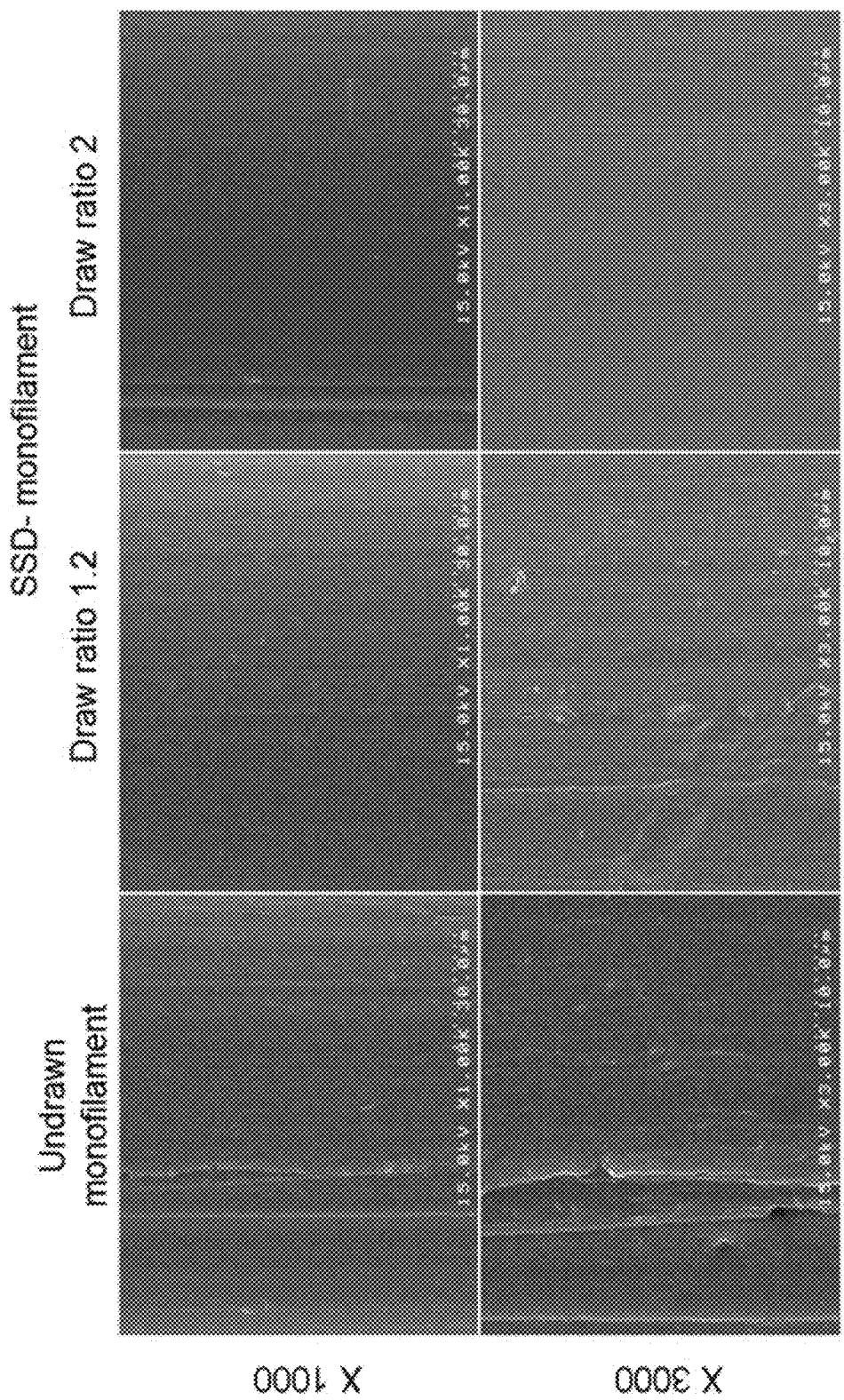
FIG. 5A shows the scanning electron microscopic (SEM) images of the surface of a polylactic acid monofilament before (undrawn) and after solid-state drawing at a draw ratio of 1.2 and 2.
Figure 5B:
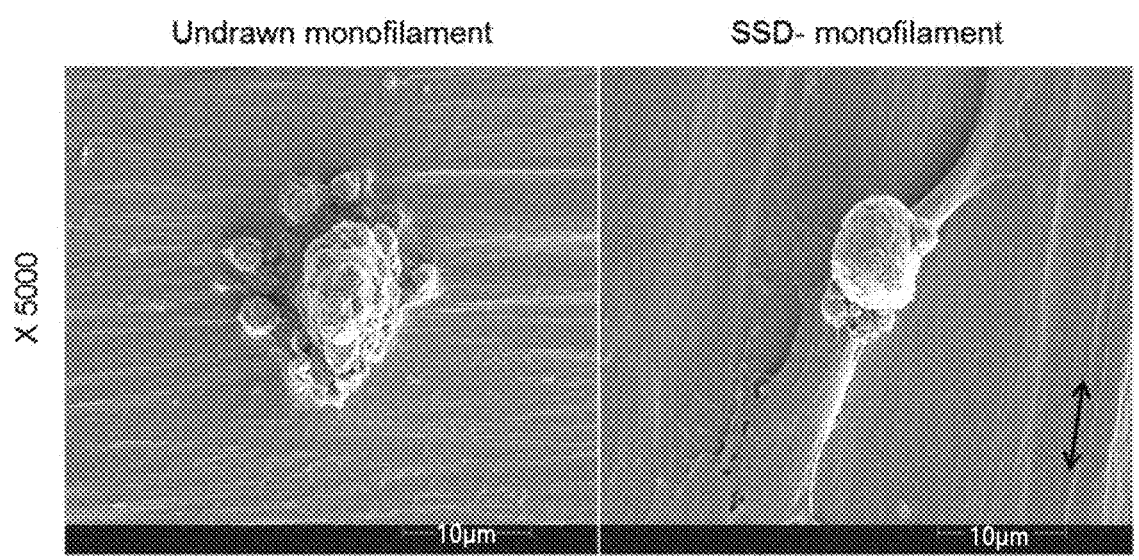
FIG. 5B shows the scanning electron microscopic (SEM) images of human umbilical vein endothelial cells (HUVECs) attached to a polylactic acid monofilament before (undrawn) and after solid-state drawing at a draw ratio of 1.2 and 2
Figure 5C:
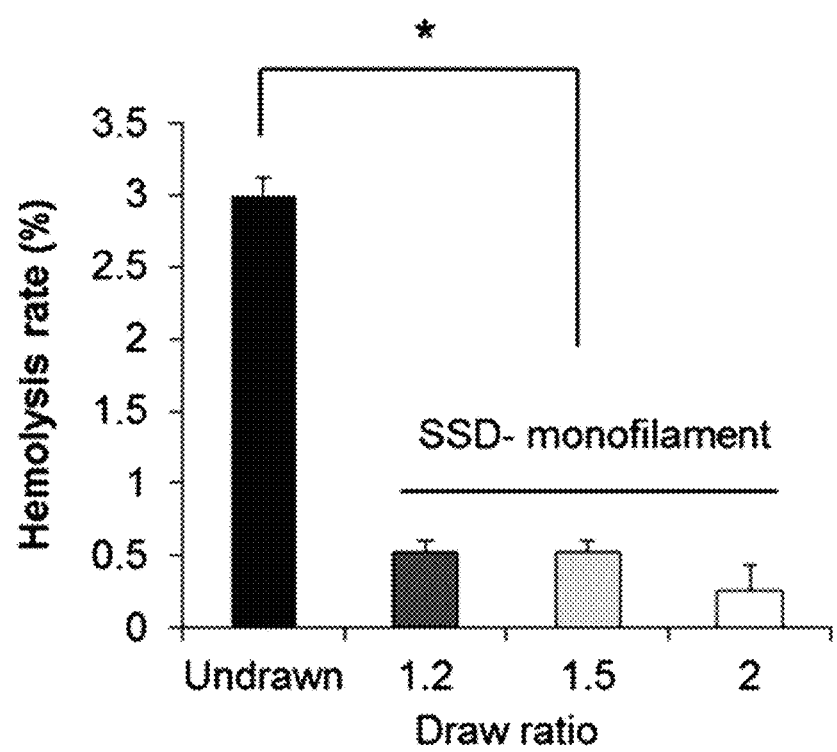
FIG. 5C shows the hemolysis rate of a polylactic acid monofilament before (undrawn) and after solid-state drawing at a draw ratio of 1.2 and 2 [in FIG. 5B, the arrow indicates the direction of solid-state drawing.

In addition to the internal changes of the solid-state drawn monofilaments, external changes were observed on their surfaces. As shown in FIGS. 5A to 5C, the undrawn polylactic acid monofilament exhibited a rough surface with defects visible at both low (×1000) and high (×3000) magnifications, whereas the solid-state drawn monofilament with a draw ratio of 1.2 showed a smoother surface and the surface of the solid-state drawn monofilament with a draw ratio of 2 was smooth and uniform with no fine defects even at the higher magnification. Accordingly, it was confirmed that the solid-state drawing according to the present disclosure can not only improve the mechanical strength of the polylactic acid monofilament through crystal orientation but also provide favorable properties for use as a biomaterial by smoothening the outer surface.

It was investigated whether the solid-state drawn monofilament is suitable for use as a vascular stent by attaching human umbilical vein endothelial cells (HUVECs) onto the monofilament [FIGS. 5B and 5C].

As shown in FIG. 5B, the HUVECs could not stably spread onto the undrawn monofilament. In contrast, they could stably adhere to the solid-state drawn monofilament and cell stretching was also possible, depending on the direction of the solid-state drawing.

FIG. 5C shows the hemolysis rates of the undrawn monofilament and solid-state drawn monofilaments with various draw ratios. All the solid-state drawn monofilaments showed significantly lower hemolysis rates than that of the undrawn monofilament (2.9±0.1). In addition, the hemolysis rates of the solid-state drawn monofilaments slightly decreased with increasing draw ratios of 1.2, 1.5 and 2 (0.5±0.1, 0.5±0.1, 0.3±0.2, respectively).

Figure 9A:
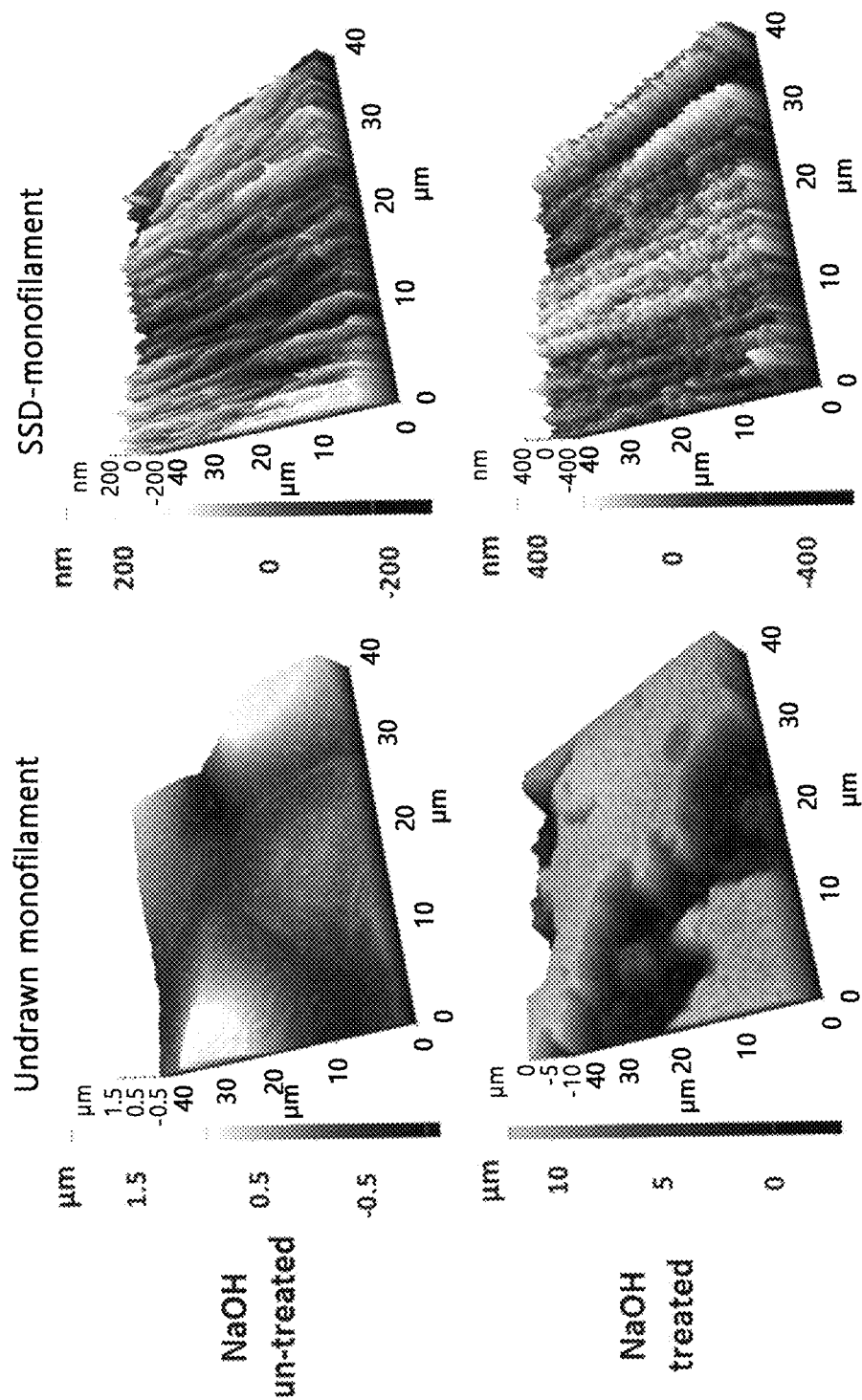
FIG. 9A shows a result of observing the surface of a solid-state drawn polylactic acid monofilament (SSD-monofilament) prepared by a method for preparing a biodegradable suture according to the present disclosure and a general polylactic acid monofilament (undrawn monofilament) by atomic force microscopy (AFM) after treating with 3 M sodium hydroxide (NaOH) for 1 hour and FIG. 9B shows a result of comparing the surface roughness of the monofilaments. In the graphs, the $R_q$ value indicates the standard deviation of the surface height of the monofilament and the $R_{pv}$ value indicates the distance between the highest peak and the lowest value (peak-to-valley distance).
Figure 9B:
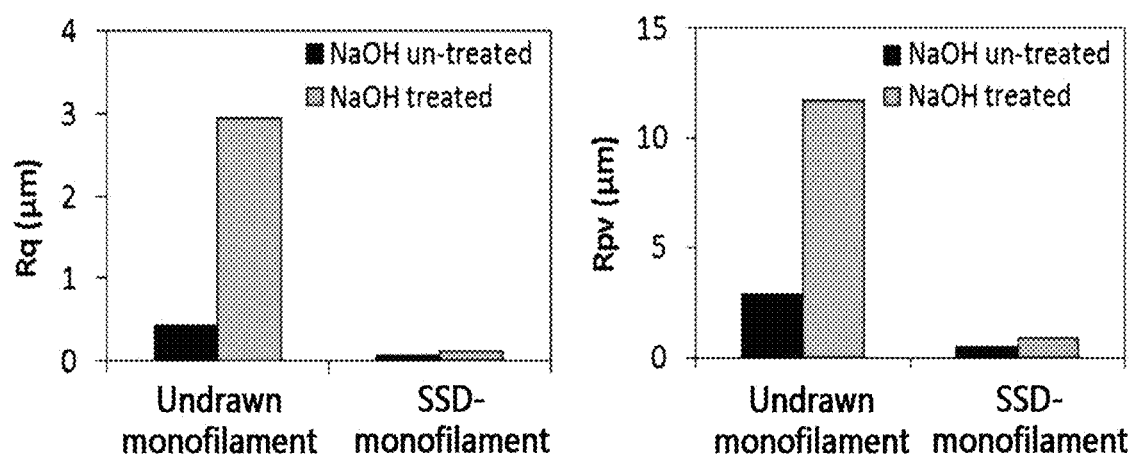

(3) Surface Chemical Properties of Polylactic Acid Monofilament Changed by Solid-State Drawing After treating the undrawn monofilament and the solid-state drawn monofilament with the strong base NaOH, changes in their surfaces and roughness were measured by atomic force microscopy (AFM). From FIG. 9A it can be seen that the general polylactic acid monofilament (undrawn monofilament) not treated with NaOH has a rough surface with a large difference in heights. In contrast, the polylactic acid monofilament (SSD-monofilament) prepared by the preparation method according to the present disclosure has a valley-shaped microstructure with little difference in heights, unlike the general polylactic acid monofilament. It is thought that the microstructure was induced by the solid-state drawing and microvalleys aligned in one direction were formed according to the drawing direction. From the result of treating the two samples with NaOH and then conducting AFM measurement under the same condition, it can be seen that a large hole was formed on the surface of the NaOH-treated undrawn monofilament and the difference in heights was enlarged. In contrast, for the NaOH-treated solid-state drawn monofilament, no distinct defect was observed on the surface and the difference in heights did not increase significantly as compared to the undrawn monofilament. To compare the change in the roughness of the polylactic acid monofilament on the basis of the AFM measurement, it can be seen that both the $R_q$ (standard deviation of heights) and $R_{pv}$ (peak-to-valley distance) values used as roughness indices were significantly lower in the solid-state drawn monofilament not treated with NaOH as compared to the undrawn monofilament not treated with NaOH, as can be seen from FIG. 9B When the undrawn monofilament was treated with NaOH, surface roughness increased greatly (2.5 μm) and the $R_{pv}$ value increased significantly (8.9 μm). In contrast, the solid-state drawn monofilament showed little increase in roughness (56 nm) and the $R_{pv}$ value remained almost constant (461 nm).

The surface characteristics of a biomaterial such as morphology and hydrophobicity/hydrophilicity play an important role in interaction with blood proteins, cells and enzymes after transplantation. The surface characteristics of the polylactic acid monofilament was analyzed to investigate how they were modified by the solid-state drawing (SSD). As a result, it was confirmed that the solid-state drawn monofilament has a smooth surface with no cracks even at higher magnification and the hydrophobicity of the solid-state drawn monofilament was increased relative to the undrawn monofilament. Also, it was observed from the AFM images that a valley-shaped microstructure can be induced on the surface of the solid-state drawn monofilament. Interestingly, the solid-state drawn monofilament having microvalleys did not show significant defects or change in roughness after the treatment with NaOH. Meanwhile, the undrawn monofilament showed higher roughness values ($R_q$ and $R_{pv}$) and the values were greatly increased after the treatment with NaOH. It is thought that the solid-state drawing leads to decreased surface free energy and roughness of the polylactic acid film. Accordingly, it was confirmed that the orientation of the polylactic acid monofilament induced by the solid-state drawing can affect its surface characteristics.

Figure 10A:
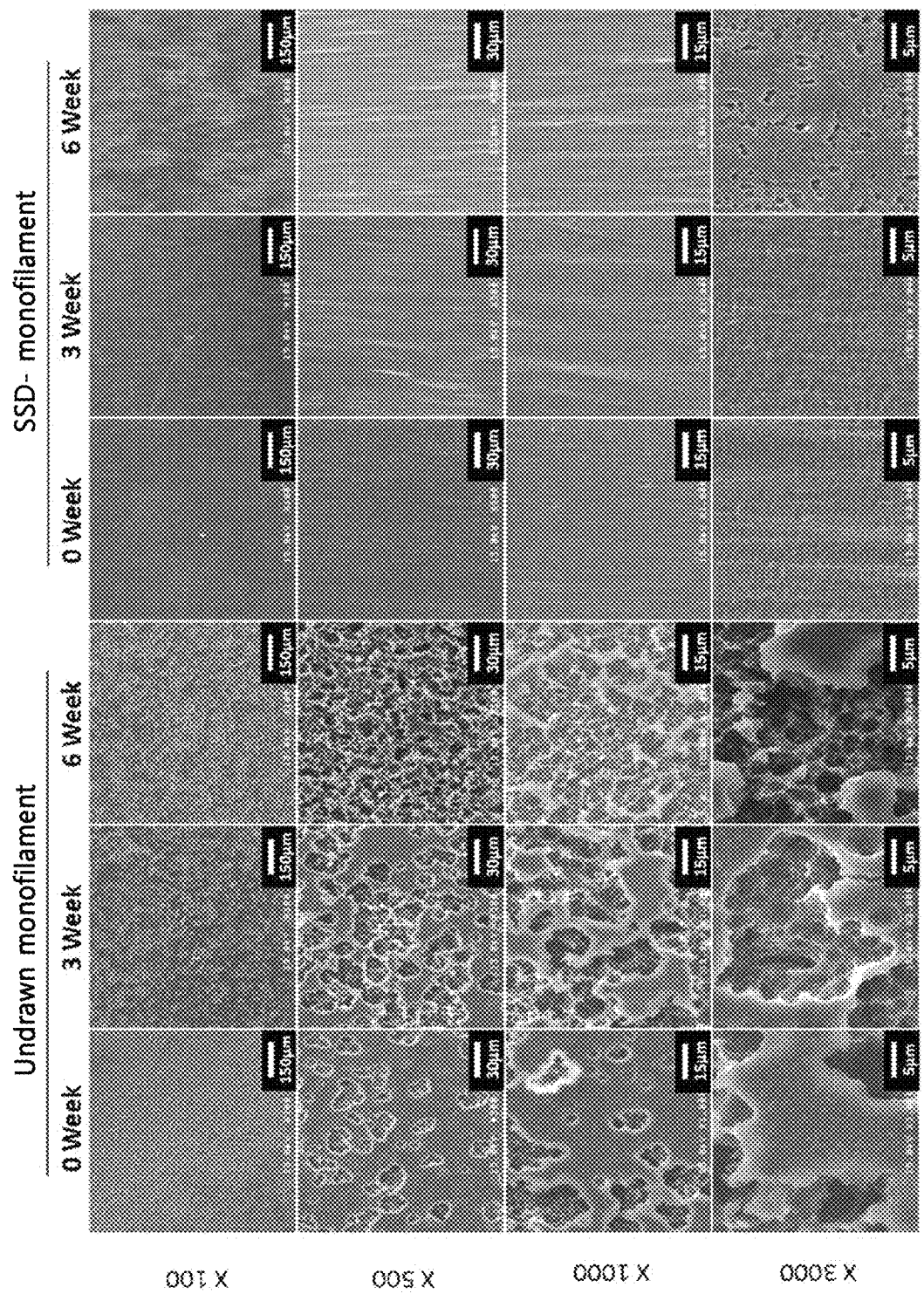
FIG. 10A shows a result of observing a solid-state drawn polylactic acid monofilament (SSD-monofilament) prepared by a method for preparing a biodegradable suture according to the present disclosure and a general polylactic acid monofilament (undrawn monofilament) in phosphate-buffered saline (PBS) at 37° C. by SEM for 6 weeks after treating with 3 M sodium hydroxide (NaOH) for 1 hour

From the SEM images shown in FIG. 10A, it can be seen that the hole on the surface of the undrawn monofilament was enlarged for 6 weeks after the treatment with NaOH, suggesting the degradation proceeded rapidly. Meanwhile, the surface of the solid-state drawn monofilament (SSD-monofilament) with a draw ratio of 2 remained almost constant during the same period and the hole was hardly detected on the monofilament surface after 6 weeks.

Figure 10B:
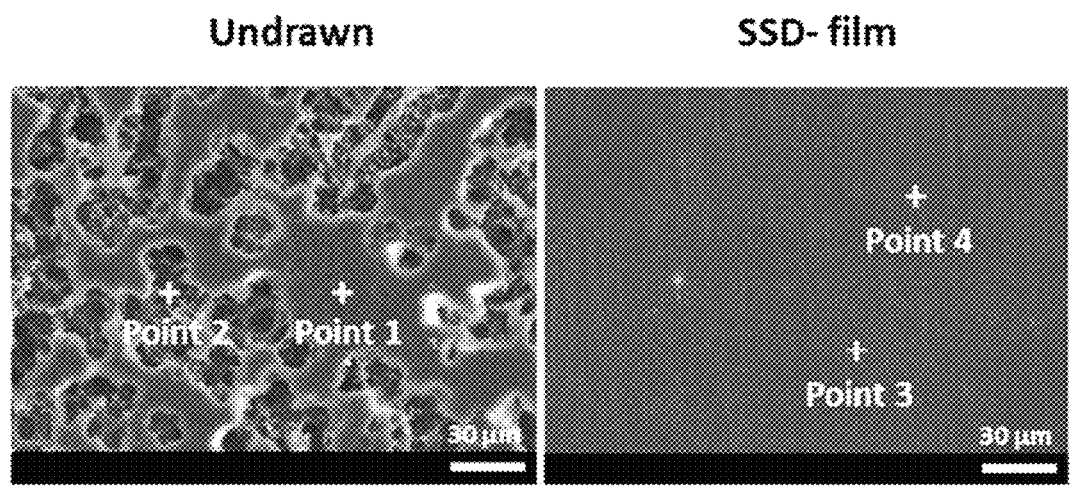
FIG. 10B shows a result of analyzing ions remaining on the surface of the monofilaments at week 6 by EDS (energy-dispersive X-ray spectroscopy).

FIG. 10B shows a result of EDS analysis conducted to investigate the cause of the damage observed on the NaOH-treated surface. For the NaOH-treated undrawn monofilament, only $Cl^-$ ion was detected in the flat region of the surface (point 1) whereas both $Na^+$ and $Cl^-$ were detected in the hole region (point 2). In contrast, no ion was detected on the entire surface (points 3 and 4)) of the NaOH-treated solid-state drawn monofilament with a draw ratio of 2.

The result of accelerated hydrolysis for 6 weeks revealed that the surface of the solid-state drawn monofilament was degraded less as compared to the undrawn monofilament. In addition, the solid-state drawn monofilament showed less hydrolysis loss in terms of weight and molecular weight. It is though that it was more difficult for the solvent to penetrate the solid-state drawn monofilament due to high crystallinity and molecular orientation. In addition, when the PLLA monofilament was treated with NaOH, which can increase the hydrophilicity of its surface, the surface of the solid-state drawn monofilament was hardly damaged by NaOH. In contrast, the undrawn monofilament was severely damaged and was degraded faster as indicated by the formation of large holes.

Annealing Process for Use of Solid-State Drawn Monofilament with High Strength as Vascular Stent Polylactic acid monofilaments with high strength and smooth surface could be fabricated through solid-state drawing as described above. In order to use the superior monofilaments for a vascular stent, an annealing process (shaped-annealing process) for preparing a spring-form monofilament was designed.

Figure 6A:
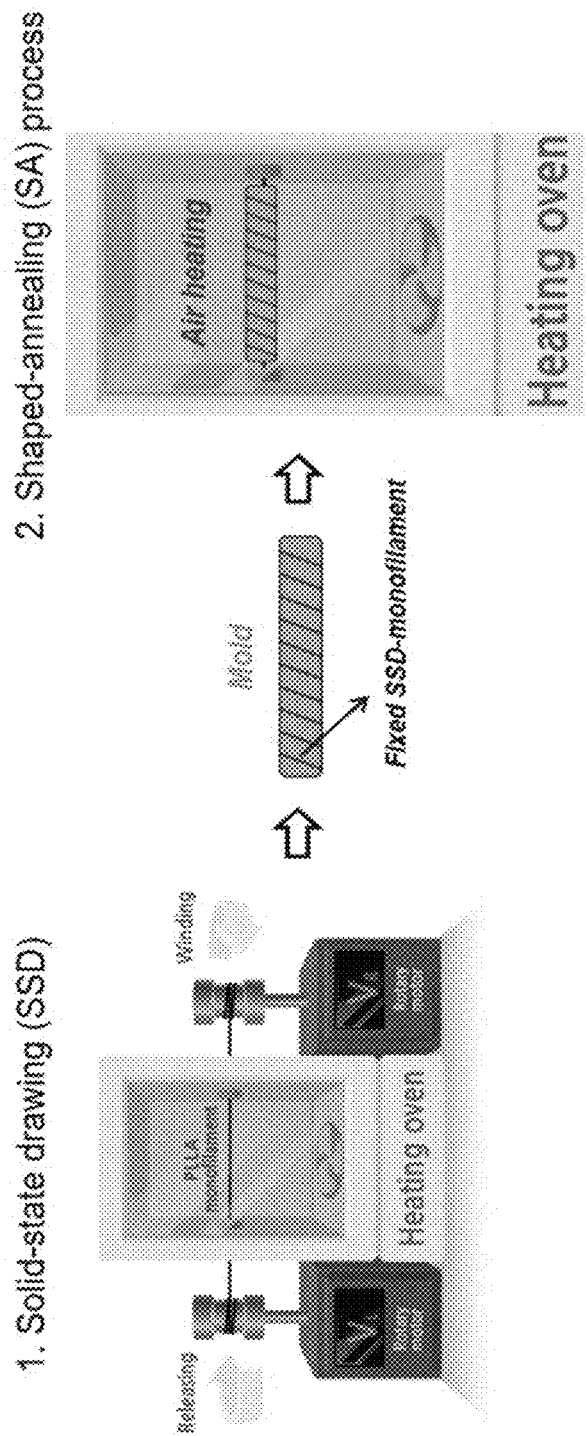
FIG. 6A schematically illustrates a continuous process of a solid-state drawing process and an annealing (shaping) process according to an according to the present disclosure and FIG. 6B shows images of stents prepared by a method for preparing a biodegradable stent of the present disclosure.
Figure 6B:
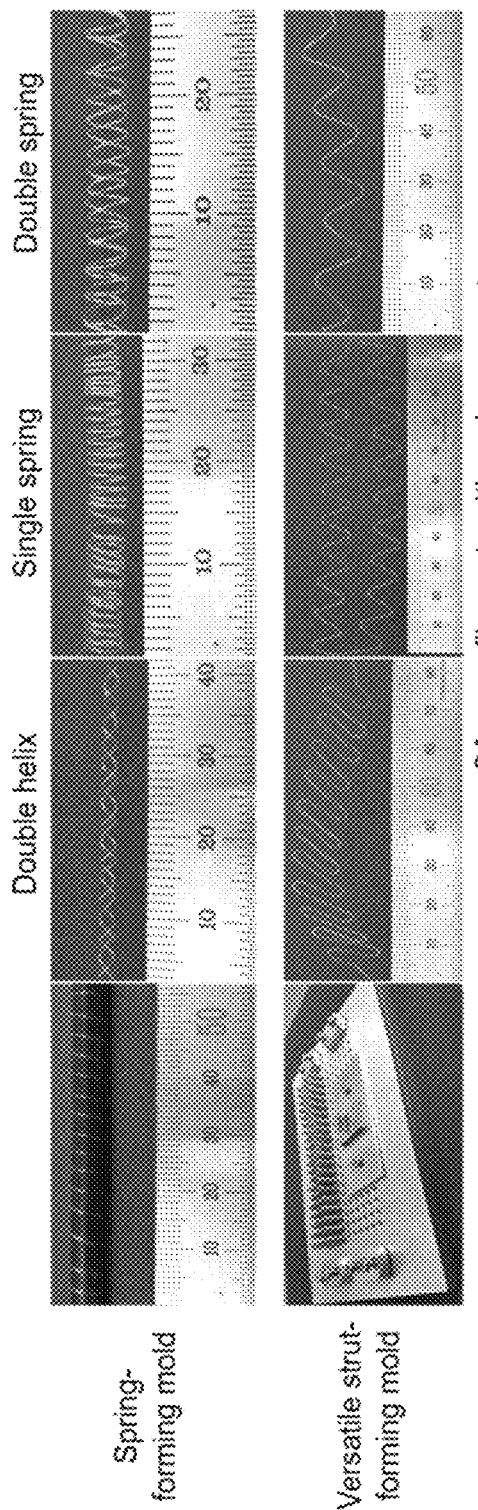

As seen from FIG. 6B, versatile strut-forming and spring-forming molds for creating stent struts of various shapes were fabricated. First, it was identified that monofilaments with varying curvatures and stent cell areas can be prepared by fixing the solid-state drawn monofilament in the versatile strut-forming mold and performing annealing at 80° C. Also, three types of solid-state drawn monofilaments could be prepared with desired shapes, i.e., double helix, single spring (composed of a single filament) and double spring (composed of two filaments), by fixing using a spring-forming and performing annealing.

Figure 7A:
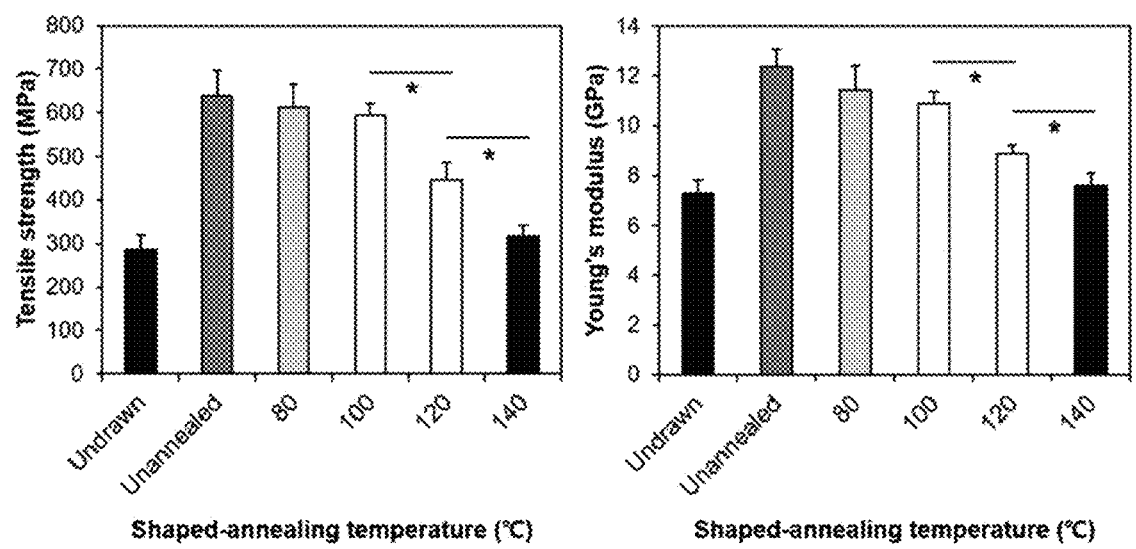
FIG. 7A shows a result of measuring the tensile strength (left) and modulus of elasticity (right) of a polylactic acid monofilament depending on an annealing temperature and FIG. 7B shows a differential scanning calorimetric (DSC) measurement result of a polylactic acid monofilament depending on an annealing temperature [data are mean±standard deviation (SD) (n=5); the asterisk denotes significant difference between two groups (p<0.05)].

Then, the annealing temperature was optimized to fix the shape of the solid-state drawn monofilament only with minimized loss of mechanical strength. As shown in FIG. 7A, no significant difference in tensile strength and modulus of elasticity was observed before and after the annealing of the solid-state drawn monofilament at 80° C. The sample annealed at 100° C. exhibited slightly decreased tensile strength and modulus of elasticity, but this was not statistically significant compared to the values for the sample before the annealing or the sample annealed at 80° C. However, the solid-state drawn monofilament annealed at 120° C. had significantly decreased tensile strength and modulus of elasticity as compared to the samples annealed at 80 and 100° C. The sample annealed at 140° C. exhibited greater reduction.

Figure 7B:
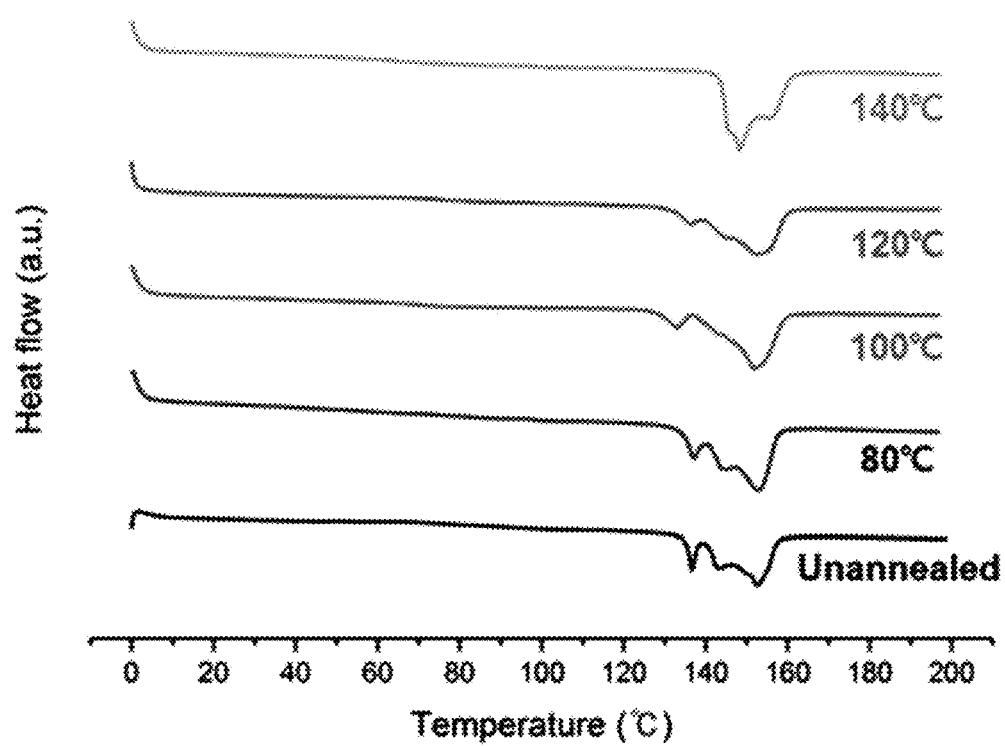

Also, as shown in FIG. 7B, three peaks around 137, 143 and 153° C. were clearly detected for the un-annealed sample and the sample annealed at 80° C. But, these three peaks were difficult to separate for the samples annealed at 100° C. or higher. With an increase in annealing temperature, the peak intensities at approximately 133 and 143° C. decreased, and the melting peak became sharper, indicating a single crystal phase. It is because recrystallization occurs as the crystals oriented during the solid-state drawing are rearranged by the thermal annealing as the temperature is increased. Accordingly, it was found that annealing performed at high temperatures of 100° C. or above can interrupt improvement of strength by destroying crystal orientation by the solid-state drawing. Therefore, the annealing temperature was optimized to 80° C. in order to shape the solid-state drawn monofilament into a stent by performing annealing without degrading its mechanical strength.

Since vascular stents are implanted inside small tubular vessels, their radial strength is very important to sufficiently withstand blood flow and vessel compression forces. Vascular stents with a weak radial strength may cause adverse events such as vessel shrinkage and collapse, restenosis and abnormal tissue remodeling. To confirm their potential, the mechanical properties of the three types of vascular stents were analyzed according to ISO 25539-2. The stents were fabricated by annealing the solid-state drawn monofilament drawn at 130° C. with a draw ratio of 2. For comparison, polylactic acid (PLLA) tubes fabricated by the existing melt extrusion method were used as controls.

Figure 8A:
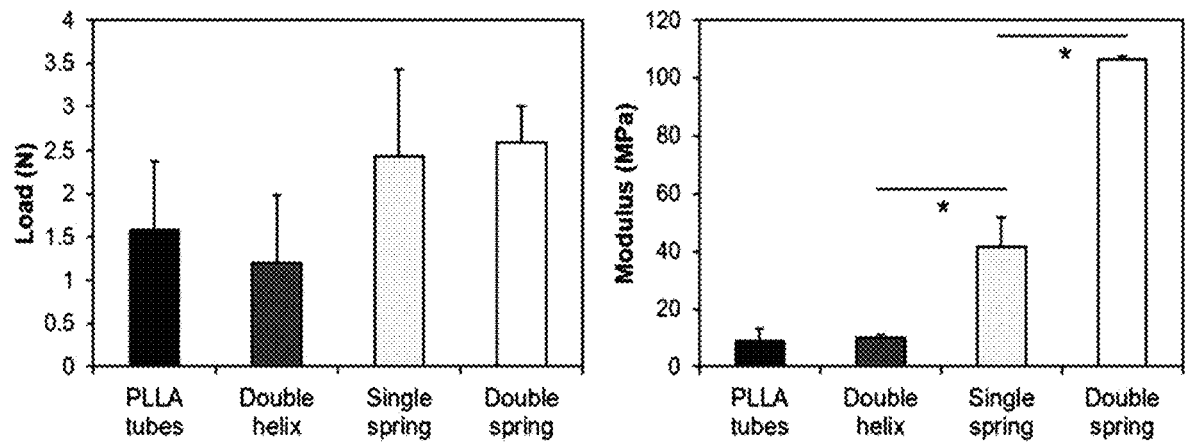
FIG. 8A shows a result of measuring the compressive load (left) and compressive modulus (right) of a polylactic acid tube prepared by the existing melt extrusion method (control) and three types of stents prepared by a preparation method according to the present disclosure (double helix, single spring and double spring)

As shown in the left graph of FIG. 8A, single or double spring-shaped stents had higher compressive loads than double helix stents, which even had a lower value than the polylactic acid tubes. It is supposed that, although the double-helix stents consisted of two monofilaments, the two fibers could not disperse the applied external forces between them because they were not in physical contact, resulting in low resistance to compression. The spring-shaped stents had higher compressive load, indicating greater resistance to circumferential forces, than the double-helix stents, because the spring-shaped stents had larger monofilament twisting angles than the double-helix stents. Though the single-spring stents had similar compressive load as the double-spring stents, the latter had slightly higher values and provided a more stable structure against external impact, as evidenced by the smaller error bar.

According to the compressive modulus graph on the right side of FIG. 8A, the double-helix stent had the smallest modulus. The single-spring stent had significantly higher modulus than double-helix stent, while the double spring stent had significantly higher modulus than the single-spring stent. Because the two spring-shaped monofilaments constituting the double spring stent physically support each other, they can absorb external compressive force together.

It is thought that it exhibits very high resistance to compression because each monofilament serves as a support. In addition to the compressive load and compressive modulus, the recovery rate was measured, which indicates to what extent the stent sample recovers its diameter after compression to 60% of its original diameter.

Figure 8B:
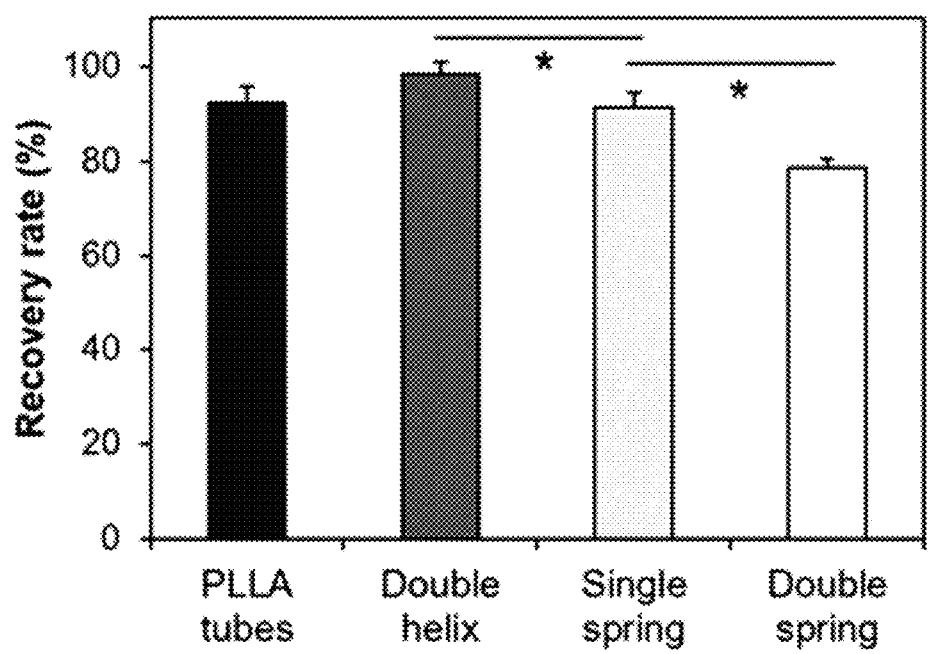
FIG. 8B shows a result of comparing an inner diameter recovery rate immediately after compression [data are mean±standard deviation (SD) (n=3); the asterisk denotes significant difference between two groups (p<0.05)].

As shown in FIG. 8B, the double-helix stent had the highest recovery rate, followed by the single-spring stent and the double-spring stent. This is opposite to the result for the compressive modulus, suggesting that more force is required for deformation as the compressive modulus of the sample is larger. The lower recovery rate means that a larger force is required to return to the original shape after deformation has occurred due to external force. Although the spring-type stents showed relatively lower recovery rate than other samples, the single-spring and double-spring stents still showed good recovery rate of 80% or higher as well as high resistance to compression. Therefore, they have characteristics favorable for vascular stents. Moreover, because the spring-shaped vascular stents could have a relatively high flexibility compared to tubular stents, this may enable their implantation in vessels with diverse curvatures and structures, and reduce pain and side effects due to vigorous activity by the patient.

The improvement of mechanical properties of biodegradable monofilaments is important to extend their biomedical application in the future. The present disclosure is directed to enhancing the mechanical properties of monofilaments to enable their use in biodegradable sutures and cardiovascular stents. To achieve this goal, polyamide (PA) and polylactic acid monofilaments with excellent mechanical strength as well as smooth surface could be successfully fabricated using the solid-state drawing method.

Additionally, a new shaped annealing process was designed to the solid-state drawn monofilament for the fabrication of cardiovascular stents with advantageous characteristics and the plausibility of fabricating vascular stents composed of monofilaments without loss of mechanical and thermal properties was presented. Various types of vascular stents could be fabricated through the annealing process and, among them, the spring-shaped stent had both high compressive resistance and recovery rate simultaneously. In conclusion, the present disclosure shows the potential of the solid-state drawn monofilament for biomedical applications.

What is claimed is:

1. A method for preparing a biodegradable stent, comprising:
    (a) providing a biodegradable filament that comprises a material which is biodegradable, that comprises polylactic acid, and that has a glass transition temperature and a melting temperature;
    (b) solid-state drawing the biodegradable filament to provide a drawn biodegradable filament, the biodegradable filament having a draw ratio that ranges from 1.1 to 5.0, that is calculated by Equation 1 below:

$$\text{Draw ratio}=(L_{SSD}/L_O)^2,$$

where $L_O$ is length of the biodegradable filament before the solid-state drawing, and $L_{SSD}$ is the length of the biodegradable filament after the solid-state drawing;
    (c) shaping the drawn biodegradable filament to provide a shaped biodegradable filament; and
    (d) annealing the shaped biodegradable filament to provide the biodegradable stent,
    wherein the solid-state drawing is performed by:
    fixing ends of the biodegradable filament between a rotatable releasing structure and a rotatable winding structure; and
    rotating the rotatable releasing structure and the rotatable winding structure in the same direction, such that the rotatable winding structure is rotated at a rotational velocity that is higher than that of the rotatable releasing structure and provides a rotational velocity ratio of the rotatable winding structure to the rotatable releasing structure that ranges from 1.01 to 3.0, and
    wherein the solid-state drawing is performed by heat-treating the biodegradable filament in a heat treatment zone present between the rotatable releasing structure and the rotatable winding structure at a heat-treating temperature ranging between the glass transition temperature and the melting temperature of the biodegradable filament by heat-treating with air maintained at the heat-treating temperature which ranges from 120 to 150° C., and with a passage speed within the heat treatment zone that ranges from 4.3 to 4.5 mm/min.

2. The method for preparing a biodegradable stent according to claim 1, wherein the biodegradable filament has a draw ratio ranging from 1.8 to 2.5.

3. A method for preparing a biodegradable stent, comprising: according to claim 2, (a) providing a biodegradable filament that comprises a material which is biodegradable, that comprises polylactic acid, and that has a glass transition temperature and a melting temperature;
    (b) solid-state drawing the biodegradable filament to provide a drawn biodegradable filament, the biodegradable filament having a draw ratio that ranges from 1.1 to 5.0, that is calculated by Equation 1 below:

$$\text{Draw ratio}=(L_{SSD}/L_O)^2,$$

where $L_O$ is length of the biodegradable filament before the solid-state drawing, and $L_{SSD}$ is the length of the biodegradable filament after the solid-state drawing;
    (c) shaping the drawn biodegradable filament to provide a shaped biodegradable filament; and
    (d) annealing the shaped biodegradable filament to provide the biodegradable stent,
    wherein the solid-state drawing is performed by:
    fixing ends of the biodegradable filament between a rotatable releasing structure and a rotatable winding structure; and
    rotating the rotatable releasing structure and the rotatable winding structure in the same direction, such that the rotatable winding structure is rotated at a rotational velocity that is higher than that of the rotatable releasing structure and provides a rotational velocity ratio of the rotatable winding structure to the rotatable releasing structure that ranges from 1.01 to 3.0, and
    wherein the solid-state drawing is performed by heat-treating the biodegradable filament in a heat treatment zone present between the rotatable releasing structure and the rotatable winding structure at a heat-treating temperature ranging between the glass transition temperature and the melting temperature of the biodegradable filament by heat-treating with air maintained at the heat-treating temperature which ranges from 120 to 150° C., and with a passage speed within the heat treatment zone that ranges from 4.3 to 4.5 mm/min, and
    wherein the annealing is performed by heat treating with air maintained at a heat treating temperature ranging from 60 to 100° C. for a time period ranging from 30 to 180 minutes.

4. The method for preparing a biodegradable stent according to claim 3, wherein the biodegradable filament has a draw ratio ranging from 1.8 to 2.5.

* * * * *